United States Patent
Vyas et al.

(10) Patent No.: US 11,938,242 B2
(45) Date of Patent: Mar. 26, 2024

(54) APPARATUS AND METHOD FOR REDUCING MALODOR ON SURFACES

(71) Applicant: The Procter & Gamble Company, Cincinnati, OH (US)

(72) Inventors: Rahul Vyas, Singapore (SG); Garima Chauhan, Singapore (SG); Madhuri Jayant Khanolkar, Singapore (SG); Gaurav Saini, Singapore (SG)

(73) Assignee: The Procter & Gamble Plaza, Cincinnati, OH (US)

( * ) Notice: Subject to any disclaimer, the term of this patent is extended or adjusted under 35 U.S.C. 154(b) by 1468 days.

(21) Appl. No.: 16/174,328

(22) Filed: Oct. 30, 2018

(65) Prior Publication Data

US 2019/0134245 A1 May 9, 2019

Related U.S. Application Data

(60) Provisional application No. 62/581,034, filed on Nov. 3, 2017.

(51) Int. Cl.
*A61L 2/20* (2006.01)
*A01N 35/02* (2006.01)
(Continued)

(52) U.S. Cl.
CPC ............... *A61L 2/20* (2013.01); *A01N 35/02* (2013.01); *A01N 35/04* (2013.01); *A01N 35/06* (2013.01);
(Continued)

(58) Field of Classification Search
CPC ..... A61L 2/20; A61L 2/28; A61L 9/01; A61L 9/037; A61L 9/122; A61L 9/127;
(Continued)

(56) References Cited

U.S. PATENT DOCUMENTS

2010/0264232 A1  10/2010  Gruenbacher
2010/0285604 A1  11/2010  Jurman
(Continued)

FOREIGN PATENT DOCUMENTS

EP   2008637 A1   12/2008
JP   2003299719 A  10/2003
(Continued)

OTHER PUBLICATIONS

ScienceDirect, Schiff Base Formation, (Year: 2023).*
(Continued)

*Primary Examiner* — Sean E Conley
*Assistant Examiner* — Brendan A Hensel
(74) *Attorney, Agent, or Firm* — Carolyn S. Powell

(57) ABSTRACT

A method of reducing malodor on surfaces including providing an apparatus in an environment including a surface wherein the surface has a malodor containing compound selected from: amine-containing compound and thiol-containing compound. The apparatus includes a volatile material having a volatile carbonyl containing compound. The volatile material is exposed to the environment such that the volatile carbonyl containing compound vaporises and deposits on the surface. The carbonyl containing compound undergoes a nucleophilic addition in the presence of the malodor containing compound.

11 Claims, 10 Drawing Sheets

(51) Int. Cl.
  *A01N 35/04* (2006.01)
  *A01N 35/06* (2006.01)
  *A01N 43/08* (2006.01)
  *A61L 2/28* (2006.01)
  *A61L 9/01* (2006.01)
  *A61L 9/03* (2006.01)
  *A61L 9/12* (2006.01)

(52) U.S. Cl.
  CPC ............. *A01N 43/08* (2013.01); *A61L 2/28* (2013.01); *A61L 9/01* (2013.01); *A61L 9/037* (2013.01); *A61L 9/122* (2013.01); *A61L 9/127* (2013.01); *A61L 2202/11* (2013.01); *A61L 2209/131* (2013.01); *A61L 2209/133* (2013.01); *A61L 2209/15* (2013.01); *A61L 2209/21* (2013.01)

(58) Field of Classification Search
  CPC ........... A61L 2202/11; A61L 2209/131; A61L 2209/133; A61L 2209/15; A61L 2209/21; A61L 9/12; A01N 35/02; A01N 35/04; A01N 35/06; A01N 43/08; B60H 3/0007
  See application file for complete search history.

(56) References Cited

U.S. PATENT DOCUMENTS

| | | |
|---|---|---|
| 2010/0314461 A1 | 12/2010 | Gruenbacher |
| 2014/0147408 A1 | 5/2014 | Williams et al. |
| 2016/0354504 A1 | 12/2016 | Sasaki |
| 2017/0274110 A1 | 9/2017 | Nwachukwu |

FOREIGN PATENT DOCUMENTS

| | | | |
|---|---|---|---|
| JP | 2013514151 | A | 4/2013 |
| JP | 2015003754 | A | 1/2015 |
| JP | 2015037574 | A | 2/2015 |
| JP | 2015525093 | A | 9/2015 |
| JP | 2016506783 | A | 3/2016 |
| JP | 2016510227 | A | 4/2016 |
| JP | 2017172568 | A | 9/2017 |
| KR | 20060038826 | A | 5/2006 |
| WO | 9816262 | A1 | 4/1998 |
| WO | WO2010120960 | A1 | 10/2010 |
| WO | WO2011075378 | A1 | 6/2011 |
| WO | WO2011084322 | A1 | 7/2011 |
| WO | WO2011084377 | A1 | 7/2011 |
| WO | WO2011084463 | A1 | 7/2011 |
| WO | WO2011084568 | A1 | 7/2011 |
| WO | WO2011084569 | A1 | 7/2011 |
| WO | WO2011084574 | A1 | 7/2011 |
| WO | WO2011084577 | A1 | 7/2011 |
| WO | WO2011137169 | A3 | 12/2011 |
| WO | WO2012078208 | A1 | 6/2012 |
| WO | WO2012078626 | A2 | 6/2012 |
| WO | WO2012097033 | A1 | 7/2012 |
| WO | WO2012097034 | A1 | 7/2012 |
| WO | WO2013154899 | A2 | 10/2013 |
| WO | WO2013176925 | A1 | 11/2013 |
| WO | WO2013188757 | A2 | 12/2013 |
| WO | WO2015050915 | A1 | 4/2015 |
| WO | WO2015050916 | A1 | 4/2015 |
| WO | WO2016145145 | A1 | 9/2016 |
| WO | WO2017030713 | A1 | 2/2017 |
| WO | WO2017030715 | A1 | 2/2017 |
| WO | WO2017030716 | A1 | 2/2017 |
| WO | WO2017030717 | A1 | 2/2017 |
| WO | 2002087360 | A2 | 11/2022 |

OTHER PUBLICATIONS

Search Report PCT/US2018/058428; 12 Pages; dated Feb. 15, 2019.

International Search Report and Written Opinion; Application Ser. No. PCT/US2018/058428; dated Apr. 5, 2019, 18 pages.

\* cited by examiner

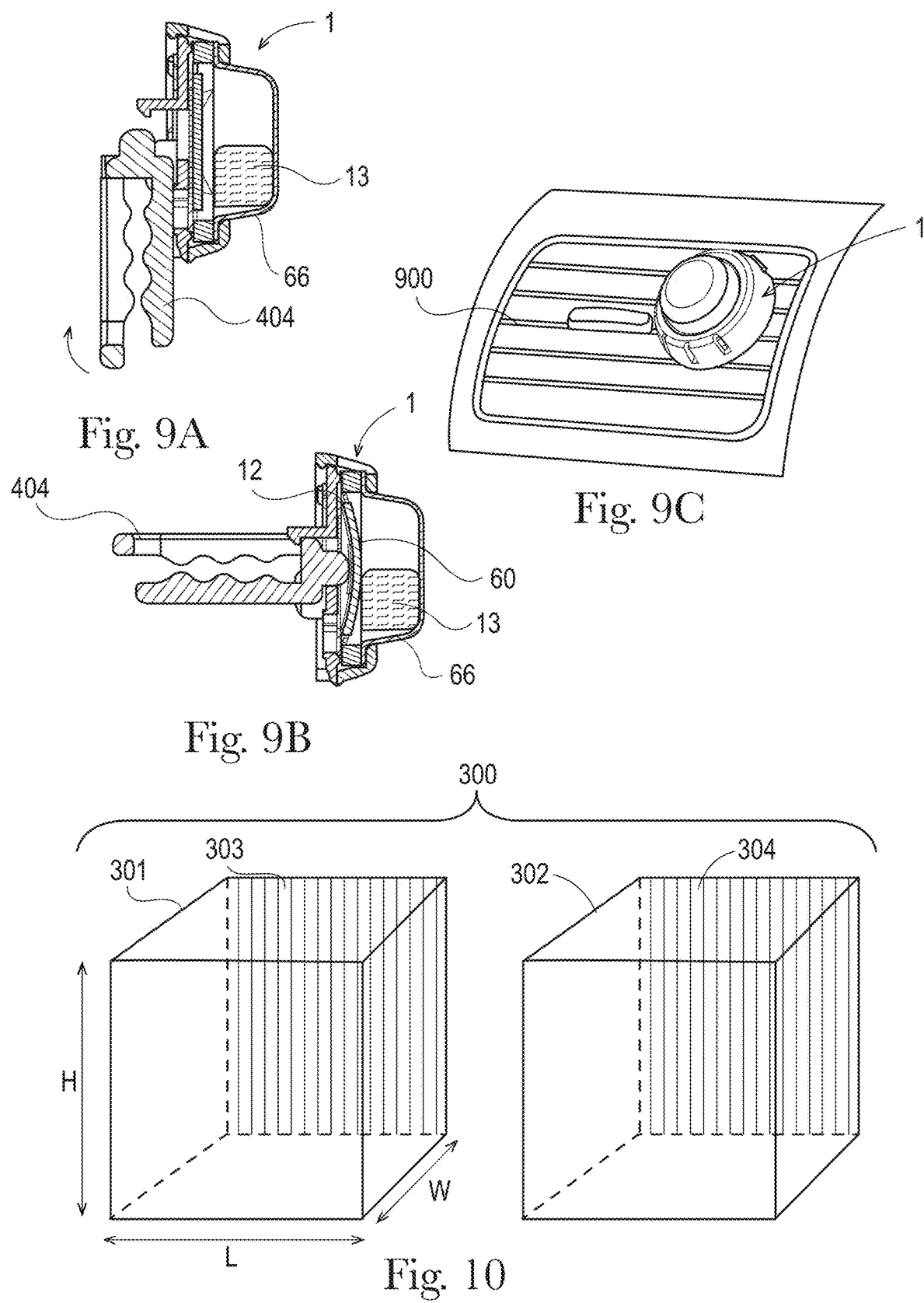

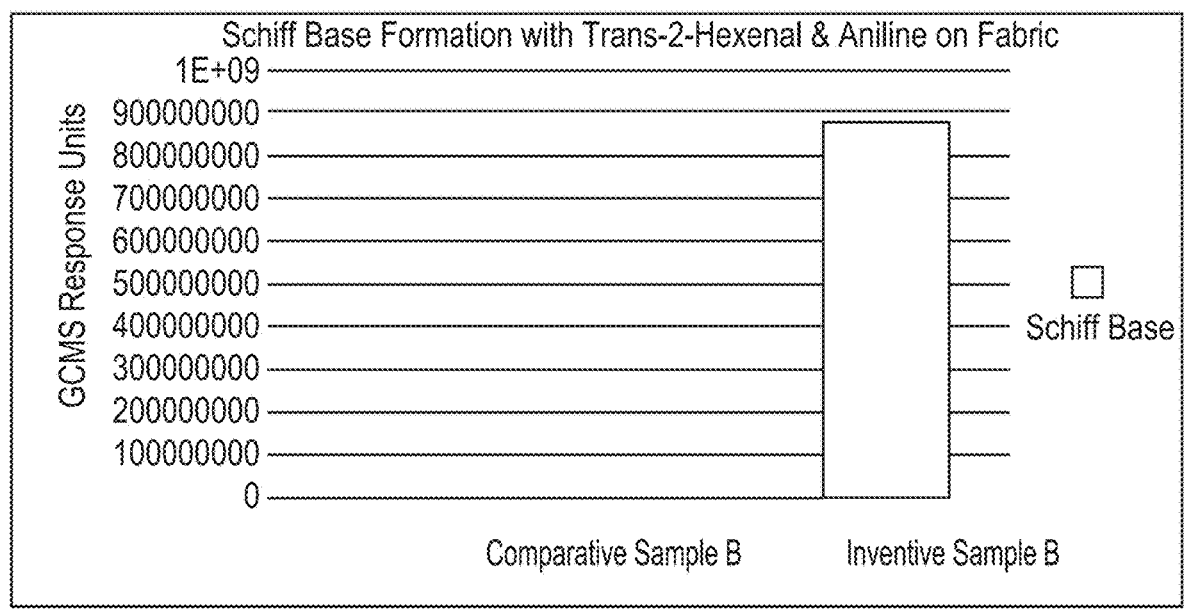
Fig. 18
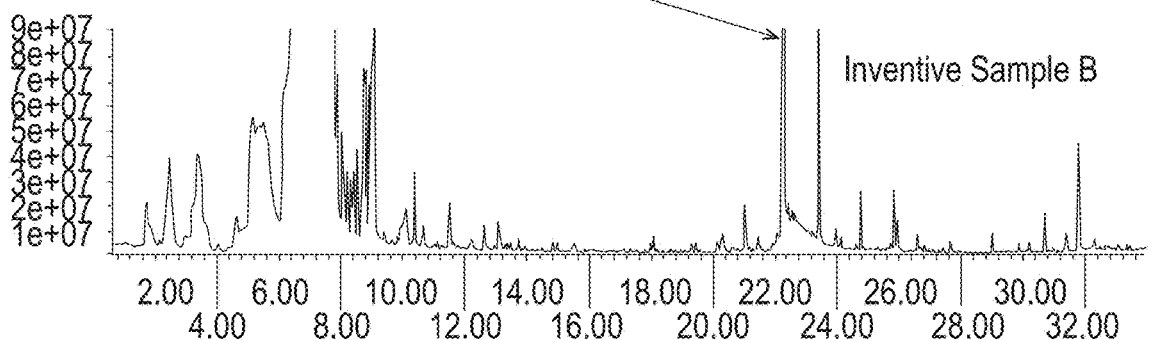
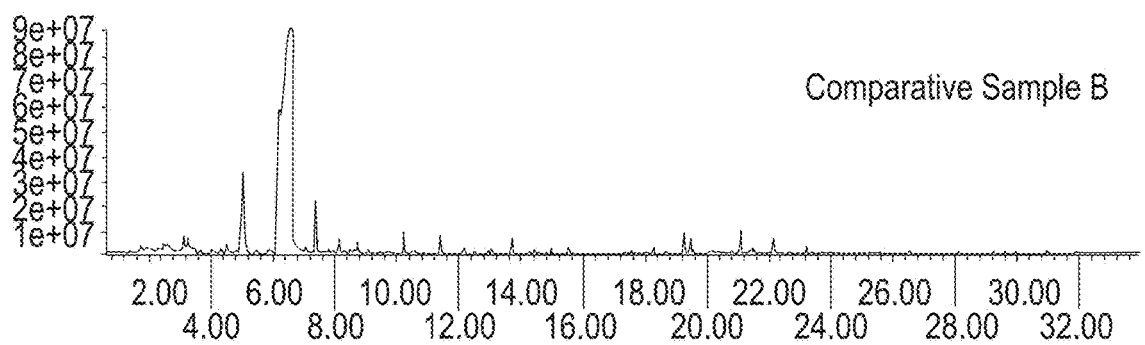
Fig. 19

APPARATUS AND METHOD FOR REDUCING MALODOR ON SURFACES

FIELD OF THE INVENTION

The present invention relates to an apparatus and a method for reducing malodors in an enclosed environment, and a method of demonstrating efficacy of a volatile material for reducing malodors on surfaces.

BACKGROUND OF THE INVENTION

Malodors in interior spaces such as in homes and vehicles typically originate from primary malodor sources (sources that actually produce the malodor), including but not limited to, tobacco smoke, food, cooking, and waste matter dispelled by humans and pets. However, malodor can also be caused by secondary malodor sources (sources that attract and/or hold malodors created by primary malodor sources) if malodor molecules are released from the secondary malodor sources into the air. For example, malodor molecules may be trapped in or on surfaces like carpet, fabric, car seat upholstery or the like and such surfaces containing the malodor molecules become a secondary malodor source. Malodor molecules may also deposit on wall surfaces, such as walls comprising wallpaper, to create additional or alternative secondary sources of malodor. These and other secondary malodor sources can create a cycle of odors and contribute to the overall malodor in an enclosed space, and are often the cause of what consumers perceive as lingering or background malodors. Air fresheners in the form of sprays, candles, oils, and gels commonly use perfume to mask malodors in the air. However, such products are generally not intended to prevent malodors from being reintroduced into the air by secondary malodor sources. As such, these known air freshening products are either unable to prevent secondary malodor sources from releasing malodors into the air or are have potentially negative side effects if applied directly to secondary malodor sources (e.g. staining on wall-paper or fabric) or indirectly by filling the space with a high concentration of the air freshening product (e.g. overwhelming scent).

Accordingly, there remains a need for a method of reducing malodor in enclosed spaces. Additionally, there remains a need for a method of reducing the ability secondary malodor sources from releasing malodors into the air. Also, it would be desirable to provide a method of demonstrating efficacy of a volatile material for reducing malodors on surfaces.

SUMMARY OF THE INVENTION

The present invention relates to a method of reducing malodor on surfaces, the method comprising the steps of:
a) providing an apparatus in an environment including a surface comprising a permeable material having disposed thereon a malodor containing compound selected from the group consisting of: amine-containing compound and thiol-containing compound, wherein the apparatus includes a volatile material having a volatile carbonyl containing compound having a vapor pressure of at least 0.025 torr at 25 degrees Celsius; and
b) exposing the volatile material to the environment such that the volatile carbonyl containing compound vaporises and deposits on at least a portion of the surface;

wherein the volatile carbonyl containing compound undergoes a nucleophilic addition in the presence of the malodor containing compound

BRIEF DESCRIPTION OF THE DRAWINGS

FIG. 9A is a side section view of a variation of an apparatus for reducing malodor on an inanimate surface according to the present invention before activation;

FIG. 9B is a side section view of the apparatus of FIG. 9A after activation;

FIG. 9C is a front perspective view of the apparatus of FIGS. 9A and 9B in use in a vehicle environment;

FIG. 10 is a schematic view of a kit for demonstrating efficacy of a volatile material for reducing malodor on a surface;

FIG. 18 is a graph plotting the GCMS response units of Comparative SampleB and Inventive Sample B; and FIG. 19 are chromatographs of Comparative Sample B and Inventive Sample B.

DETAILED DESCRIPTION OF THE INVENTION

Figure 1:
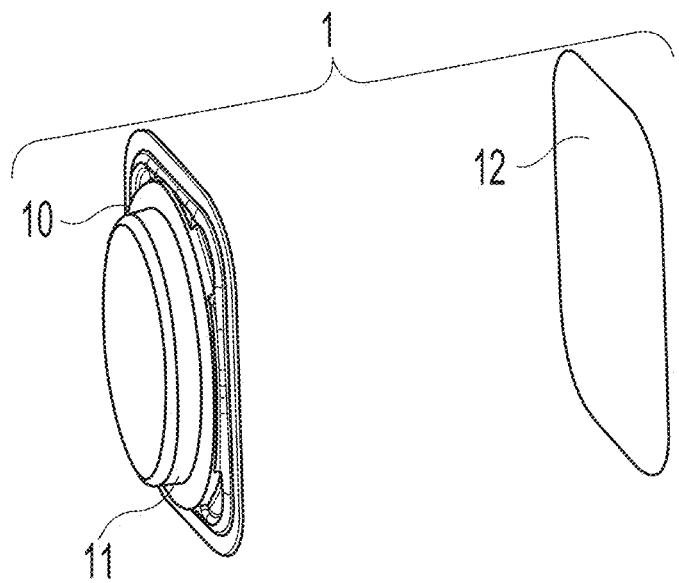
FIG. 1 is a perspective view of components of an apparatus for reducing malodor on an inanimate surface according to the present invention.

It has been found that the materials making up and/or included in enclosed spaces play an important role in the existence of odors in the air. Specifically, malodor compounds such as amines and thiols are often absorbed by certain materials, such as permeable materials and are reemitted into the air causing a lingering malodor during periods of time when malodor is not otherwise being generated. It has also been surprisingly found that volatile carbonyl containing compounds which can evaporate in passive air flow conditions continuously can adsorb onto surfaces and help neutralize malodor compounds, which can prevent them from being emitted back into the air over time.

The present invention relates to a method and apparatus for reducing malodor on surfaces, typically inanimate surfaces, in an environment, particularly within an enclosed space. The method and apparatus are suitable for various uses, including but not limited to, air freshening, deodorization, odor elimination, malodor counteraction, pest control, insect control, insect repelling, medicines/medicaments, disinfectants, sanitization, mood enhancement, aromatherapy aid, or any other use which requires a volatile material that acts to condition, modify, or otherwise change the atmosphere or the environment. For the purposes of this disclosure, but without intending to limit the scope of the invention, the method will be described as a method for reducing malodor from surfaces using an optimized composition of volatile carbonyl containing compounds that is permitted to vaporize from an apparatus and is not delivered by aerosol means. The apparatus of the present invention can be energized or non-energized.

"Non-energized" means that the apparatus is passive and does not required to be powered by a source of external energy. In particular, the apparatus does not need to be powered by a source of heat, gas or electrical current. The apparatus 1 may also be configured as an energized device. An exemplary energized device may be an electrical device. The energized device may be an electrical wall plug or battery operated air freshener having a wick and/or a membrane as described in the above to transport a freshening composition and/or evaporate a freshening composition therefrom; or other heating devices (e.g. devices powered by chemical reactions such as catalyst fuel systems; solar powered devices, etc.).

A technical effect of vaporizing a volatile carbonyl containing compound from the apparatus of the present invention is that it can be deposited on the surface in a continuous way. Having the volatile carbonyl containing compound deposited on a material allows for nucleophilic addition between the volatile carbonyl containing compound and the malodor containing compound, thereby producing a reaction product neutralizing the malodor containing compound as shown in Equation 1 below.

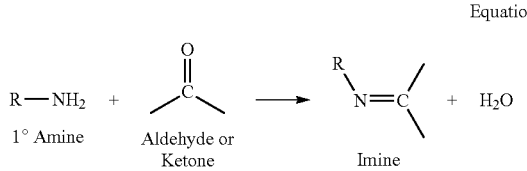

Equation 1

In Equation 1, an amine containing compound such as, a primary amine, R—NH2, is shown as an example of a malodor containing compound. The volatile carbonyl containing compound may be an aldehyde or a ketone having the respective chemical structure shown below:

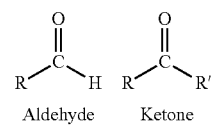

Aldehyde    Ketone

When an aldehyde or a ketone reacts with an amine containing compound, a Schiff base is formed. The Schiff base is an imine compound having the following general structure, and which is generally less odorous relative to an amine containing compound.

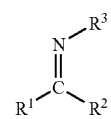

Further, aldehydes and/or ketones may also react with thiol containing compounds to form thiol acetals, hemi thiolacetals, and thiol esters in vapor and/or liquid phase. Thiol containing compounds generate sulphur-based odors.

The present invention can reduce and/or eliminate the need to provide an energy source to deliver a volatile material for reducing malodor, and reduces and/or prevents malodor through neutralization of the malodor containing compound at surfaces on which the malodor containing compound is deposited.

The following terms are defined as set forth herein. Terms not defined should be given their ordinary meaning as understood by a skilled person in the relevant art.

As used herein, the term "carbonyl containing compound" refers to a compound comprising the following structure:

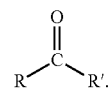

wherein R is an alkyl group and R' is selected from the group consisting of: hydrogen, an substituted or unsubstituted aryl group.

As used herein, the term "desorption" refers to a phenomenon whereby a substance is released from or through a surface.

As used herein, the term "interior space" refers to a finite volume of space in a residential, commercial or vehicle environment.

As used herein, the term "interior surfaces" refers to surfaces of objects in an interior space. Such objects may include but is not limited to, walls, ceilings, floors, wall dividers, windows, doors, trim, area rugs, carpeting, wall, hangings, vents, beds, chairs, toilets, refrigerators, kitchen cabinets, sinks, trash cans, curtains, towels, clothes, car seats, sofas, furniture, or the like.

As used herein, the term "malodor containing compound" refers to a compound selected from the group consisting of: amine-containing compound and thiol-containing compound.

As used herein, the term "membrane" refers to a semi-permeable material which allows some components of matter to pass through but stops other components. Of the components that pass through, the membrane moderates the permeation of components i.e. some components permeate faster than other components. Such components may include molecules, ions or particles.

As used herein, the term "neutralize" or "neutralization" refers to the ability of a compound or product to reduce or eliminate malodor containing compounds. Odor neutralization may be partial, affecting only some of the malodor containing compounds in a given context, or affecting only a part of a malodor containing compound. A malodor containing compound may be neutralized by chemical reaction resulting in a new chemical entity, by sequestration, by chelation, by association, or by any other interaction rendering the malodor containing compound less malodorous or non-malodorous. Odor neutralization may be distinguished from odor masking or odor blocking by a change in the malodor containing compound, as opposed to a change in the ability to perceive the malodor without any corresponding change in the conditions of the malodor containing compound.

As used herein, the term "permeable material" refers to any material that allows liquids or gases to pass through, and includes, but is not limited to, drywall, wall paper, wood, vinyl, plastic, plaster, wallboard, fabrics, upholstery, paper, wovens, natural polymers, synthetic polymers and inorganic materials and mixtures thereof. The permeable material may also include residue formed on any inanimate surface, and includes but is not limited to dust particles or grease on the inanimate surface.

As used herein, the term "inanimate surface" refers to surfaces including but not limited to fabrics, carpets, household surfaces such as countertops, floors, garbage cans, ceilings, walls, carpet padding, air filters, and the like.

As used herein, the term "volatile carbonyl containing compound" refers to a carbonyl containing compound suitable for use in non-energized systems, wherein the carbonyl containing compound comprises a vapor pressure of greater than or equal to 0.025 torr at 25 degrees Celsius.

As used herein, the term "volatile material" refers to a material that is vaporizable at room temperature and atmospheric pressure without the need of an additional energy source. The volatile material may be a composition comprises entirely of a single volatile material or entirely of a volatile material mixture (i.e. the mixture has more than one volatile component). Further, it is not necessary for all of the component materials of the composition to be volatile. Any suitable volatile material in any amount or form, including a liquid, solid, gel or emulsion, may be used. Materials suitable for use herein may include non-volatile compounds, such as carrier materials (e.g., water, solvents, etc.). It should also be understood that when the volatile material is described herein as being "delivered", "emitted", or "released", this refers to the volatilization of the volatile component thereof, and does not require that the non-volatile components thereof be emitted.

As used herein, the term "vaporize" or "vaporization" refers to a phase transition of a substance or a compound from a solid and/or liquid phase to vapor.

Method

Generally, the method of the present invention includes providing an apparatus including a volatile carbonyl material (described in more detail below) in an environment that includes an inanimate surface. For example, the volatile material may be disposed in an apparatus, such as the air freshening apparatus 1 shown in FIG. 1.

The inanimate surface comprises a material having a malodor containing compound disposed thereon. The malodor containing compound may be chosen from the group consisting of: amine-containing compound and thiol-containing compound. The volatile carbonyl containing compound is permitted to vaporize from the apparatus and deposit on the inanimate surface. The volatile carbonyl containing compound undergoes a nucleophilic addition in the presence of the malodor containing compound to neutralize the malodor containing compound thereby reducing the malodor on the inanimate surface. An effect is that the inanimate surface does not become a secondary malodor source. Thus, providing an apparatus according to the present invention in an enclosed space enables reduction of malodor on inanimate surfaces in a passive and continuous manner, and consequently acts to reduce or eliminate secondary malodor sources.

The method may be useful for continuous removal of malodor in enclosed environments, such as for example, interior spaces in residences, buildings and vehicles. The malodor may be any undesirable odor, such as, for example, odors from urine, fecal material, cooking, smoking or the like.

Volatile Material

The method of the present invention can be implemented using an air freshening composition, wherein the air freshening composition comprise up to 100%, about 4% to about 100%, about 15% to about 100%, about 65% to 86%, of the volatile material by weight of the air freshening composition.

An important feature of the volatile material of the present invention is that it can measurably neutralize malodor (e.g. by gas chromatograph) rather than merely covering up or masking the malodor. Neutralization, in this context, can have the benefit of providing both short and long term reduction in malodors. In the short term, a malodor neutralizer can reduce the level of malodors in the air that are currently being sensed by, for example, a human. In the longer term, certain neutralizers can help prevent malodors from remaining on surfaces, creating secondary sources of malodor. Thus, by selecting and employing specific malodor neutralizers it is possible to prevent reintroduction of malodors into an environment from surfaces, which can effectively reduce or eliminate lingering or background malodors.

The volatile material of the present invention may comprise a mixture of carbonyl containing compounds. The mixture of carbonyl containing compounds may be present in an amount of from about equal to or greater than 0.01% to about less than or equal to 100%, in an amount from about 0.01% to 50%, from about 1% to 40%, from about 4% to 25%, from about less than or equal to 5% to equal to or less than 25% by weight of the volatile material. An effect of having less than 25% by weight of the carbonyl containing compounds is to enable formulation space for adding optional ingredients described hereinafter such as perfume raw materials to provide a hedonic experience.

The vapor pressure of the volatile carbonyl containing compounds may be greater than or equal to 0.025 torr, about 0.025 torr to about 30 torr, measured at 25 degrees Celsius. The vapor pressure of individual volatile carbonyl containing compounds can be calculated using the Advanced Chemistry Development Labs ("ACD") (Toronto, Canada) VP computational model, version 14.02 providing vapor pressure (VP) values at 25 degrees Celsius expressed in unit of torr. When the volatile carbonyl containing compound and the malodor containing compound deposit on the same interior surfaces in an interior space, the volatile carbonyl containing compound will generally undergo a nucleophilic reaction in the presence of the malodor containing compound generate a reaction product that is less odorous than the malodor containing compound.

The volatile carbonyl containing compound may be selected from the group consisting of: volatile aldehydes, ketones and mixtures thereof. Exemplary volatile aldehydes and ketones are listed in the following description and are named according to the method of naming organic chemical compounds as recommended by the International Union of Pure and Applied Chemistry (IUPAC).

The carbonyl containing compound may comprise volatile aldehydes. Aldehydes that are partially volatile may be considered a volatile aldehyde as used herein. As described above, volatile aldehydes react with amine-containing compounds, following the path of Schiff-base formation. Volatiles aldehydes also react with thiol-containing compounds, forming thiol acetals, hemi thiolacetals, and thiol esters in vapor and/or liquid phase. Exemplary volatile aldehydes which may be used include, but are not limited to, aldehydes as shown in Table 1 below. The carbonyl containing compound may also comprise ketones. Exemplary ketones which may be used in the volatile material include, but are not limited to ketones shown in Table 2 below.

Without wishing to be bound by theory, it is believed that a carbonyl containing compound selected from Tables 1 and 2 below are more reactive with a malodor containing compound and therefore are more effective in reducing malodor. Further, a carbonyl containing compound from Tables 1 and 2 may comprise a lower difference between lowest unoccupied molecular orbital (LUMO) energy of the carbonyl containing compound and highest occupied molecular orbital (HOMO) energy of a malodor containing compound and therefore the carbonyl containing compound may be more reactive relative to carbonyl containing compounds which have a higher difference.

TABLE 1

| CAS | IUPAC Name | Vapor Pressure (torr) @ 25 degrees Celsius |
|---|---|---|
| 04-55-2 | (E)-3-phenylprop-2-enal | 0.080 |
| 100-52-7 | Benzaldehyde | 0.13 |
| 122-03-2 | 4-propan-2-ylbenzaldehyde | 0.031 |
| 123-11-5 | 4-methoxybenzaldehyde | 0.021 |
| 557-48-2 | (2E,6Z)-nona-2,6-dienal | 0.18 |
| 6728-26-3 | (E)-hex-2-enal | 10.66 |
| 5392-40-5 | (2E)-3,7-dimethylocta-2,6-dienal | 0.13 |
| 2363-89-5 | (E)-oct-2-enal | 0.99 |
| 21662-13-5 | (2E,6Z)-dodeca-2,6-dienal | 0.004 |
| 2463-53-8 | non-2-enal | 0.21 |
| 1335-66-6 | 2,4,6-trimethylcyclohex-3-ene-1-carbaldehyde; 3,5,6-trimethylcyclohex-3-ene-1-carbaldehyde | 2.64 |
| 33885-52-8 | 3-(6,6-dimethyl-4-bicyclo[3.1.1]hept-3-enyl)-2,2-dimethylpropanal | 0.028 |
| 124-19-6 | Nonanal | 0.37 |
| 65405-70-1 | (E)-dec-4-enal | 0.35 |
| 106-72-9 | 2,6-dimethylhept-5-enal | 0.48 |
| 2277-19-2 | (Z)-non-6-enal | 0.22 |
| 3613-30-7 | 7-methoxy-3,7-dimethyloctanal | 0.040 |
| 6784-13-0 | 3-(4-methylcyclohex-3-en-1-yl)butanal | 0.11 |
| 106-23-0 | 3,7-dimethyloct-6-enal | 0.14 |
| 19009-56-4 | 2-methyldecanal | 0.053 |
| 68039-49-6 | 2,4-dimethylcyclohex-3-ene-1-carbaldehyde | 0.73 |
| 112-45-8 | undec-10-enal | 0.019 |
| 71077-31-1 | 4,8-dimethyldeca-4,9-dienal | 0.019 |
| 124-13-0 | Octanal | 1.14 |
| 112-44-7 | Undecanal | 0.037 |
| 112-31-2 | Decanal | 0.12 |
| 143-14-6 | undec-9-enal | 0.011 |
| 62439-41-2 | 6-methoxy-2,6-dimethylheptanal | 0.130 |
| 33885-51-7 | 3-(6,6-dimethyl-4-bicyclo[3.1.1]hept-3-enyl)propanal | 0.039 |

TABLE 2

| CAS | IUPAC Name | Vapor Pressure (VP), torr @ 25° C. |
|---|---|---|
| 1125-21-9 | 2,6,6-trimethylcyclohex-2-ene-1,4-dione | 0.158 |
| 10373-78-1 | 4,7,7-trimethylbicyclo[2.2.1]heptane-2,3-dione | 0.0817 |
| 1193-79-9 | 1-(5-methylfuran-2-yl)ethanone | 0.301 |
| 765-70-8 | 3-methylcyclopentane-1,2-dione | 0.978 |
| 98-86-2 | 1-phenylethanone | 0.299 |
| 600-14-6 | pentane-2,3-dione | 26.416 |
| 4077-47-8 | 4-methoxy-2,5-dimethylfuran-3-one | 0.103 |
| 3658-77-3 | 4-hydroxy-2,5-dimethylfuran-3-one | 0.032 |
| 1196-01-6 | (1S,5S)-2,6,6-trimethylbicyclo[3.1.1]hept-2-en-4-one | 0.0773 |
| 18309-32-5 | (1R,5R)-2,6,6-trimethylbicyclo[3.1.1]hept-2-en-4-one | 0.0773 |

TABLE 2-continued

| CAS | IUPAC Name | Vapor Pressure (VP), torr @ 25° C. |
|---|---|---|
| 78-59-1 | 3,5,5-trimethylcyclohex-2-en-1-one | 0.15 |
| 2758-18-1 | 3-methylcyclopent-2-en-1-one | 2.741 |
| 2244-16-8 | (5S)-2-methyl-5-prop-1-en-2-ylcyclohex-2-en-1-one | 0.0656 |
| 6485-40-1 | (5R)-2-methyl-5-prop-1-en-2-ylcyclohex-2-en-1-one | 0.0656 |
| 141-79-7 | 4-methylpent-3-en-2-one | 8.757 |
| 99-49-0 | 2-methyl-5-prop-1-en-2-ylcyclohex-2-en-1-one | 0.0656 |
| 1072-83-9 | 1-(1H-pyrrol-2-yl)ethanone | 0.11 |
| 89-82-7 | (5R)-5-methyl-2-propan-2-ylidenecyclohexan-1-one | 0.0934 |
| 2550-26-7 | 4-phenylbutan-2-one | 0.0557 |
| 2308-18-1 | 3-methylbutyl 3-oxobutanoate | 0.167 |
| 513-86-0 | 3-hydroxybutan-2-one | 1.92 |
| 81786-73-4 | (Z)-3,4,5,6,6-pentamethylhept-3-en-2-one | 0.0275 |
| 4906-24-5 | 3-oxobutan-2-yl acetate | 2.069 |
| 105-45-3 | methyl 3-oxobutanoate | 1.543 |
| 141-97-9 | ethyl 3-oxobutanoate | 0.89 |
| 5524-05-0 | (2R,5R)-2-methyl-5-prop-1-en-2-ylcyclohexan-1-one | 0.107 |
| 7764-50-3 | 2-methyl-5-prop-1-en-2-ylcyclohexan-1-one | 0.107 |
| 5948-04-9 | (2S,5S)-2-methyl-5-prop-1-en-2-ylcyclohexan-1-one | 0.107 |
| 55739-89-4 | 2-ethyl-4,4-dimethylcyclohexan-1-one | 0.25 |
| 25304-14-7 | 1-(3,3-dimethylcyclohexyl)ethanone | 0.287 |
| 36977-92-1 | (2S,5S)-5-methyl-2-propan-2-ylcyclohexan-1-one | 0.256 |
| 89-80-5 | (2S,5R)-5-methyl-2-propan-2-ylcyclohexan-1-one | 0.256 |
| 65443-14-3 | 2,2,5-trimethyl-5-pentylcyclopentan-1-one | 0.0261 |
| 873-94-9 | 3,3,5-trimethylcyclohexan-1-one | 0.582 |
| 4884-24-6 | 2-cyclopentylcyclopentan-1-one | 0.0588 |
| 546-80-5 | (1S,4R,5R)-4-methyl-1-propan-2-ylbicyclo[3.1.0]hexan-3-one | 0.323 |
| 16587-71-6 | 4-(2-methylbutan-2-yl)cyclohexan-1-one | 0.0649 |
| 76-22-2 | 4,7,7-trimethylbicyclo[2.2.1]heptan-3-one | 0.225 |
| 110-93-0 | 6-methylhept-5-en-2-one | 1.277 |
| 111-13-7 | octan-2-one | 1.725 |
| 7787-20-4 | (1S,4R)-2,2,4-trimethylbicyclo[2.2.1]heptan-3-one | 0.463 |
| 110-43-0 | heptan-2-one | 4.732 |
| 1195-79-5 | 2,2,4-trimethylbicyclo[2.2.1]heptan-3-one | 0.463 |
| 541-85-5 | 5-methylheptan-3-one | 2.444 |
| 106-68-3 | octan-3-one | 1.504 |

Table 3 shows a mixture of volatile aldehydes suitable for use in the method of the present invention, the mixture is referred to herein as Accord A.

TABLE 3

Accord A

| CAS No. | Material Name | Weight % by weight of the Volatile Material | VP (torr) @ 25° C. |
|---|---|---|---|
| 6728-26-3 | (E)-hex-2-enal | 1 to 4 | 10.66 |
| 1335-66-6 | 2,4,6-trimethylcyclohex-3-ene-1-carbaldehyde; 3,5,6-trimethylcyclohex-3-ene-1-carbaldehyde | 4 to 8 | 2.64 |
| 124-13-0 | octanal | 7 to 12 | 1.14 |
| 68039-49-6 | 2,4-dimethylcyclohex-3-ene-1-carbaldehyde | 10 to 20 | 0.73 |
| 106-72-9 | 2,6-dimethylhept-5-enal | 10 to 20 | 0.48 |
| 2277-19-2 | (Z)-non-6-enal | 0.1 to 0.3 | 0.22 |
| 557-48-2 | (2E,6Z)-nona-2,6-dienal | 0.3 to 1.0 | 0.18 |
| 100-52-7 | benzaldehyde | 8 to 13 | 0.13 |
| 5392-40-5 | (2E)-3,7-dimethylocta-2,6-dienal | 7 to 12 | 0.13 |
| 112-31-2 | decanal | 10 to 20 | 0.12 |
| 30772-79-3 | 4,7-Methanoindan-1-carboxaldehyde | 10 to 20 | 0.05 |
| | Total by weight of the Volatile Material | 100% | |

Table 4 shows a further mixture of volatile aldehydes suitable for use in the method of the present invention, the mixture is referred to herein as Accord B.

TABLE 4

Accord B

| CAS | Material Name | Wt % by weight of the Volatile Material | VP (torr) @ 25° C. |
|---|---|---|---|
| 6728-26-3 | (E)-hex-2-enal | 0.5 to 2.0 | 10.66 |
| 124-13-0 | octanal | 3 to 10 | 1.14 |
| 110-41-8 | 2-methylundecanal | 1 to 5 | 0.015 |
| 100-52-7 | benzaldehyde | 10 to 20 | 0.13 |
| 106-72-9 | 2,6-dimethylhept-5-enal | 3 to 8 | 0.48 |
| 68039-49-6 | 2,4-dimethylcyclohex-3-ene-1-carbaldehyde | 9 to 15 | 0.73 |
| 124-19-6 | nonanal | 1 to 3 | 0.37 |
| 1335-66-6 | 2,5,6-trimethylcyclohex-3-ene-1-carbaldehyde | 5 to 10 | 2.64 |
| 557-48-2 | (2E,6Z)-nona-2,6-dienal | 0.2 to 1.2 | 0.182 |
| 112-31-2 | decanal | 7 to 15 | 0.12 |
| 5392-40-5 | (E)-3,7-dimethylocta-2,6-dienal | 10 to 20 | 0.13 |
| 112-45-8 | undec-10-enal | 1 to 5 | 0.019 |
| 112-54-9 | dodecanal | 1 to 6 | 0.007 |
| 123-11-5 | 4-methoxybenzaldehyde | 10 to 20 | 0.021 |
| | Total by weight of the Volatile Material | 100% | |

Providing a volatile material having a mixture of volatile aldehydes in the above specified ranges in a method according to the present invention and an effective reduction of malodor on surfaces is demonstrated in Example II.

Optional Ingredients

The air freshening composition may, optionally, include odor masking agents, odor blocking agents, and/or diluents. "Odor blocking" refers to the ability of a compound to dull the human sense of smell. "Odor-masking" refers to the ability of a compound to mask or hide a malodorous compound. Odor-masking may include a compound with a non-offensive or pleasant smell that is dosed such it limits the ability to sense a malodorous compound. Odor-masking may involve the selection of compounds which coordinate with an anticipated malodor to change the perception of the overall scent provided by the combination of odorous compounds. Exemplary diluents include dipropylene glycol methyl ether, and 3-methoxy-3-methyl-1-butanol, and mixtures thereof.

The air freshening composition may also, optionally, include perfume raw materials that solely provide a hedonic benefit (i.e. perfume raw materials which do not neutralize malodors yet provide a pleasant fragrance).

Apparatus

The method of the present invention can be implemented using an apparatus such as an air freshening apparatus. It is contemplated that the apparatus may be configured for use in a variety of applications to deliver volatile materials to the atmosphere and/or a surface as long as the volatile material is evaporated from the apparatus. For the purposes of this disclosure, but without intending to limit the scope of the invention, the apparatus is described as a non-energized apparatus.

For example, the step of providing an apparatus may comprise providing a reservoir for a liquid phase or a solid phase of the volatile material. The apparatus 1 may also comprise a delivery member configured to contain a liquid phase of the volatile material and allow the liquid phase of the volatile material to evaporate therefrom. The delivery member may include a wick, a breathable membrane, gel, porous or semi-porous substrate including a felt pad. An exemplary delivery member may be a membrane which is a semi-permeable material which allows some components of matter to pass through but stops other components. Of the components that pass through, the membrane moderates the permeation of components i.e. some components permeate faster than other components. Such components may include molecules, ions or particles. FIG. 1 shows an exploded view of an apparatus 1 according to the present invention. The apparatus 1 comprises a container 10 having a reservoir 11 for containing a liquid phase or a solid phase of a volatile material. The container 10 may be made of a substantially vapor impermeable substrate designed to resist diffusion of a vapor phase of the volatile material from the apparatus 1 prior to its intended use. For example, the container 10 may be made of metal, glass, ceramic, porcelain, tile and plastic including but not limited to thermoplastics and other known materials suitable for thermoforming, injection molding and blow molding. A membrane 12 may be disposed within the container 10 adjacent to the reservoir 11 for allowing a vapor phase of the volatile material to pass through. The membrane 12 may be a microporous membrane and comprise an average pore size of about 0.01 to about 0.06 microns, from about 0.01 to about 0.05 microns, about 0.01 to about 0.04 microns, about 0.01 to about 0.03 microns, about 0.02 to about 0.04 microns, about 0.02 microns. Further, the membrane 12 may be filled with any suitable filler and plasticizer known in the art. Fillers may include finely divided silica, clays, zeolites, carbonates, charcoals, and mixtures thereof. The microporous membrane 12 may be filled with about 50% to about 80%, by total weight, of silica, alternatively about 60% to about 80%, about 70% to about 80%, about 70% to about 75%. A thickness of the membrane 12 may be about 0.01 mm to about 1 mm, between about 0.1 mm to 0.4 mm, about 0.15 mm to about 0.35 mm, about 0.25 mm.

Still further, an evaporative surface area of the microporous membrane 12 may be about 2 $cm^2$ to about 100 $cm^2$, about 2 cm2 to about 25 $cm^2$, about 10 $cm^2$ to about 50 $cm^2$, about 10 $cm^2$ to about 45 $cm^c$, about 10 $cm^2$ to about 35 $cm^2$, about 15 $cm^2$ to about 40 $cm^2$, about 15 $cm^2$ to about 35 $cm^2$, about 20 $cm^2$ to about 35 $cm^2$, about 30 $cm^2$ to about 35 $cm^2$, about 35 $cm^2$. Suitable microporous membranes for the present invention include a microporous, ultra-high molecular weight polyethylene (UHMWPE) optionally filled with silica as described in U.S. Pat. No. 7,498,369. Such UHMWPE microporous membranes include Daramic™ V5, available from Daramic, Solupor®, available from DSM (Netherlands), and Teslin™, available from PPG Industries, and combinations thereof. Although the apparatus 1 is described using a membrane, it will be appreciated that a wick may also be used in the apparatus and the method according to the present invention. Similarly, the apparatus 1 may also be configured with a heating element or a fan to facilitate vaporization of the volatile material from the apparatus 1.

Figure 2:
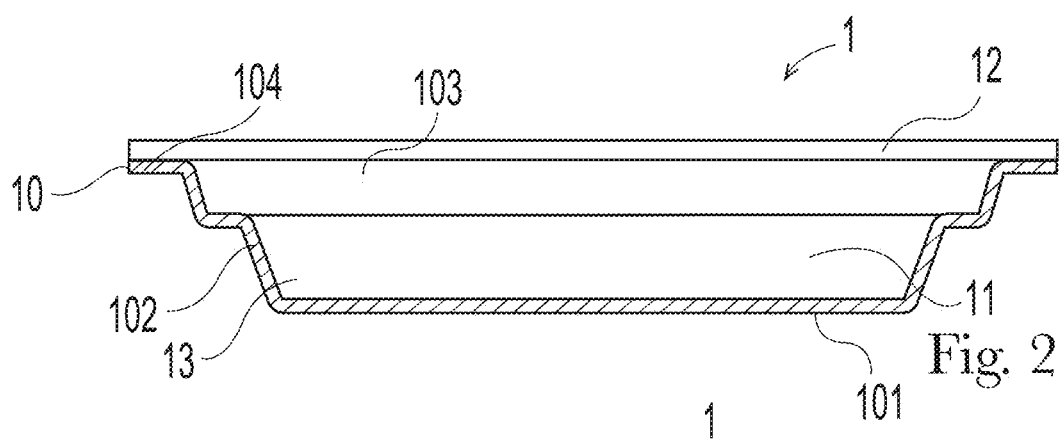
FIG. 2 is a side section view of the apparatus shown in FIG. 1 in a horizontal orientation when the apparatus is placed on a support.
Figure 3:
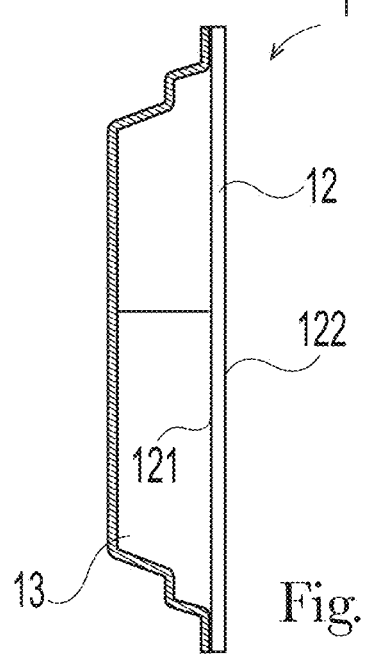
FIG. 3 is a side section view of the apparatus shown in FIG. 1 in a vertical orientation when the apparatus is placed on a support.

FIG. 2 shows a schematic view of the assembled apparatus 1 of FIG. 1 in a horizontal orientation with a volatile material 13 disposed within the container 10. Referring to FIG. 2, the container 10 may comprise an end wall 101, side walls 102 and an opening 103 at a periphery 104 of the side walls 102 which define the reservoir 11. For example, if the container 12 is made of thermoplastics, the membrane 12 may be attached to the periphery 104 of the container 10 using conventional heat staking methods to contain the volatile material 13 within the reservoir 11. The apparatus 1 may be may be configured for use in any desired orientation, including but not limited to a vertical orientation such as shown in FIG. 3. FIG. 3 shows a side schematic view of the apparatus 1 of FIG. 1 wherein the apparatus 1 is substantially the same as the apparatus 1 of FIG. 1 except that the membrane 12 comprises a first surface 121 disposed in fluid communication with the volatile material 13 and a second surface 122 facing the environment and away from the volatile material 13.

Figure 4:
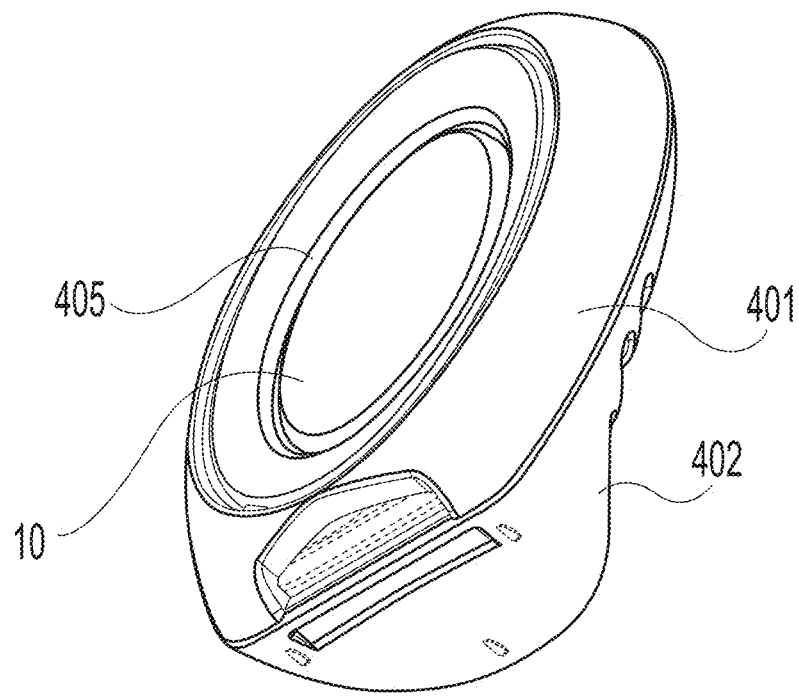
FIG. 4 is a front perspective view of a variation of an apparatus for reducing malodor on an inanimate surface according to the present invention.
Figure 5:
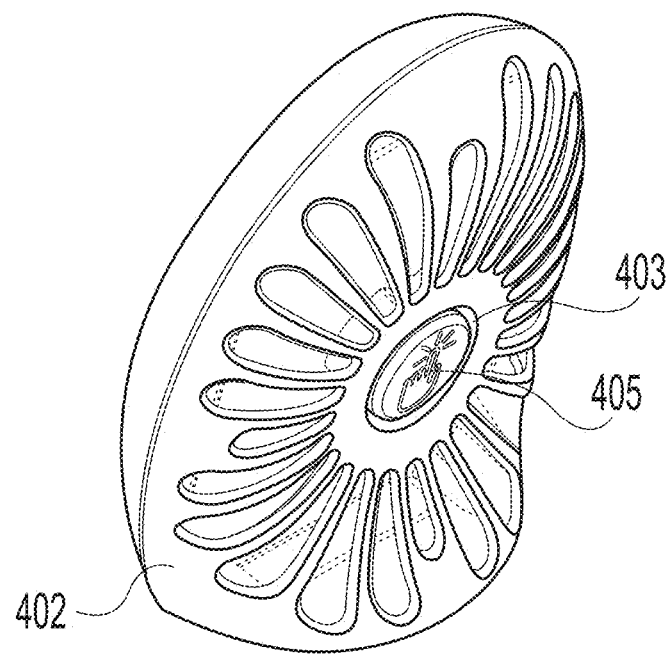
FIG. 5 is a rear perspective view of the apparatus of FIG. 4.
Figure 6:
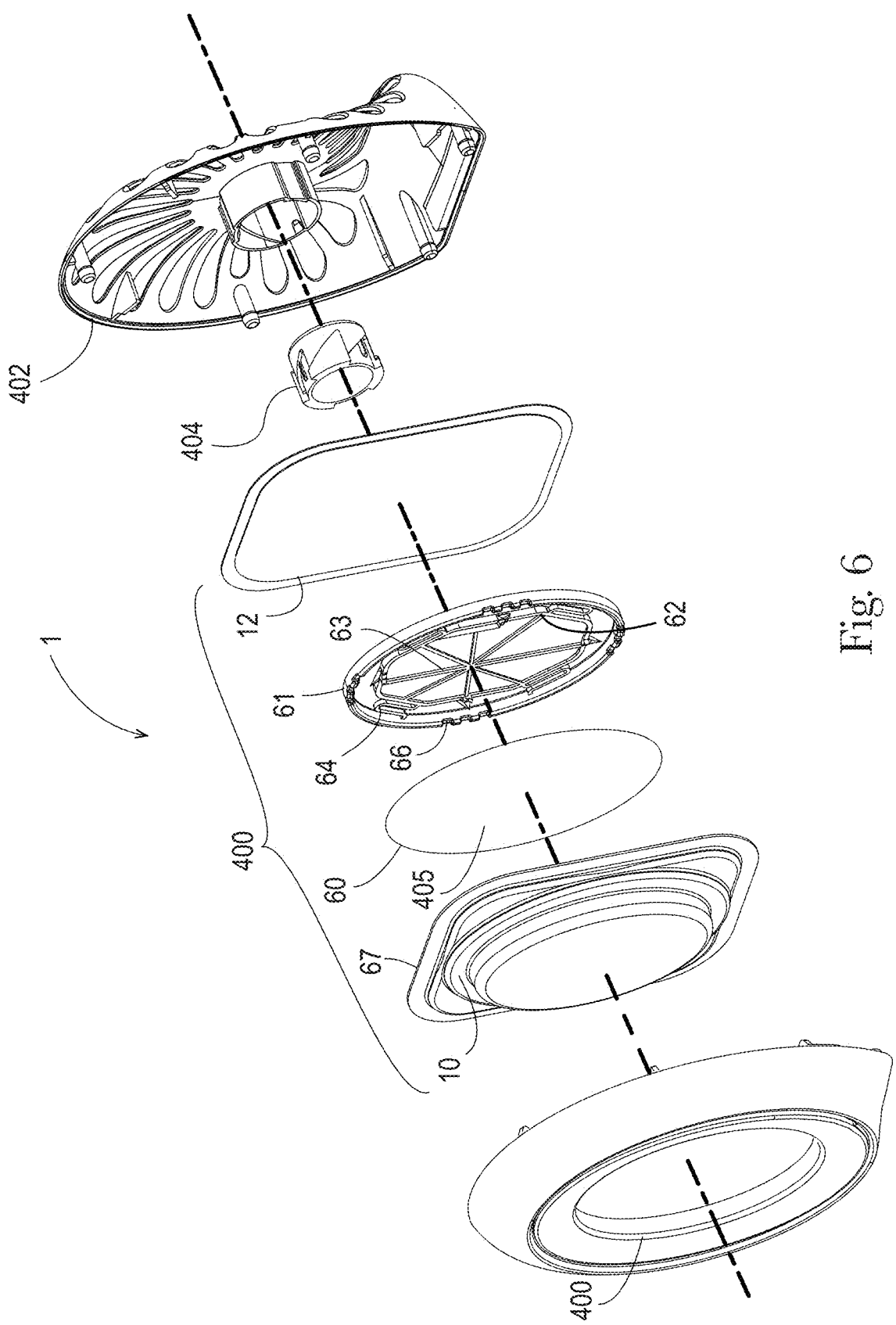
FIG. 6 is a perspective view of components of the apparatus of FIG. 4.

FIG. 4 shows a front perspective view of a further example of an apparatus 1 according to the present invention and FIG. 5 shows a rear perspective view of the apparatus 1 before use. FIG. 6 shows internal components of the apparatus 1 of FIGS. 4 and 5. The apparatus 1 of FIGS. 4, 5 and 6 comprise substantially the same features as the apparatus 1 of FIG. 1 with additional components described as follows.

Referring to FIGS. 4 and 5, the apparatus 1 comprises a housing 40 having a front cover 401 and a rear frame 402, the front cover 401 and the rear frame 402 defining an interior space. The rear frame 402 is provided with a frame opening 403 (hereinafter "opening") located substantially in the centre of the rear frame 402. An actuator 404 movable relative to the housing 40 is provided for activating the apparatus 1. The actuator 404 may be, for example, a push button 404 (hereinafter "button") disposed within the opening 403 and is movable with respect to the rear frame 402 for enabling a user to activate the apparatus 1. The container 10 containing the volatile material 13 is located within the housing 40. The front cover 401 comprises a window 405 configured for displaying the container 10.

When the volatile material 12 is a liquid volatile composition, the apparatus 1 may comprise a rupturable substrate 60 sealably attached to and covering the reservoir 11 to prevent the volatile material 13 from being released until the apparatus 1 is activated. The rupturable substrate 60 may be ruptured to release the volatile material 13 by actuating a rupture mechanism 61 positioned adjacent to the rupturable substrate 60. The rupture mechanism 61 comprises a movable member 62 movably attached to an outer frame 63 by a resilient member 64. The resilient member 64 may be formed of one or more springs 65. One or more rupture elements 66 are arranged within the rupture mechanism 61 to puncture holes in the rupturable substrate 60. The rupture element 66 may be a pin. As described in the above for FIG. 1, the membrane 12 may be sealably attached to a flange 67 located at the periphery 104 of the container 10. The membrane 12 encloses the container 10, the volatile material 12, the rupturable substrate 60, and the rupture mechanism 61. The membrane 12 may be configured to flex when a pressure or an actuation force is applied on the membrane 12 through the button 404.

Figure 7:
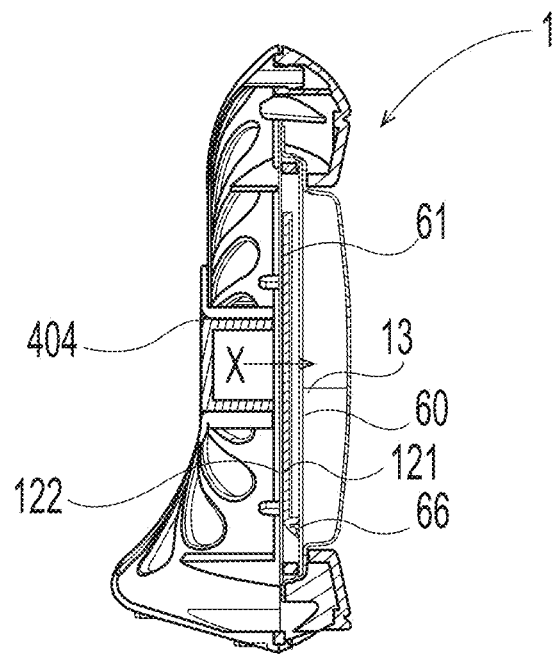
FIG. 7 is a side section view of the apparatus of FIG. 4.

Referring to FIG. 7, to activate the apparatus 1, a user depresses the button 404 until it makes contact with the rupture mechanism 61 (through the deflection of the membrane 12 in a direction X towards the front end of the container), and the rupture elements 66 on the rupture mechanism 61 pierce the rupturable substrate 60. Once the rupturable substrate 60 is pierced, the volatile material 13 flows out of the container 10, wets the membrane 12 and is then delivered to the atmosphere surroundings through evaporation from the membrane 12. Specifically, wetting of the membrane 12 occurs when a liquid phase of the volatile material 13 comes into contact with and spreads on at least a part of the first surface 121 of the membrane 12. The membrane 12 is configured to prevent the liquid phase of the volatile material 13 from flowing out of the membrane 12 but enables vaporization of a vapor phase of the volatile material 13 from the second surface 122 so that the volatile material 13 is delivered to the environment.

The volatile material 13 may be delivered through a wick wherein the wick may be configured to have various different shapes and sizes. For example, the wick may have a cylindrical or an elongate cube shape. The wick may be defined by a length and a diameter or width, depending on the shape. The wick may have various lengths. For example, the length of the wick may be in the range of about 1 millimeter ("mm") to about 100 mm, or from about 5 mm to about 75 mm, or from about 10 mm to about 50 mm. The wick may have various diameters or widths. For example, diameter or width of the wick may be at least 1 mm, or at least 2 mm, or at least 3 mm, or at least 4 mm. A wick may exhibit a density. The wick density may be in the range of about 0.100 grams/cm$^3$ ("g/cc") to about 1.0 g/cc. A wick may comprise a porous or semi-porous substrate. The wick may be composed of various materials and methods of construction, including, but not limited to, bundled fibers which are compressed and/or formed into various shapes via overwrap (such as a non-woven sheet over-wrap) or made of sintered plastics such as PE, HDPE or other polyolefins. For example, the wick may be made from a plastic material such as polyethylene or a polyethylene blend.

Figure 8:
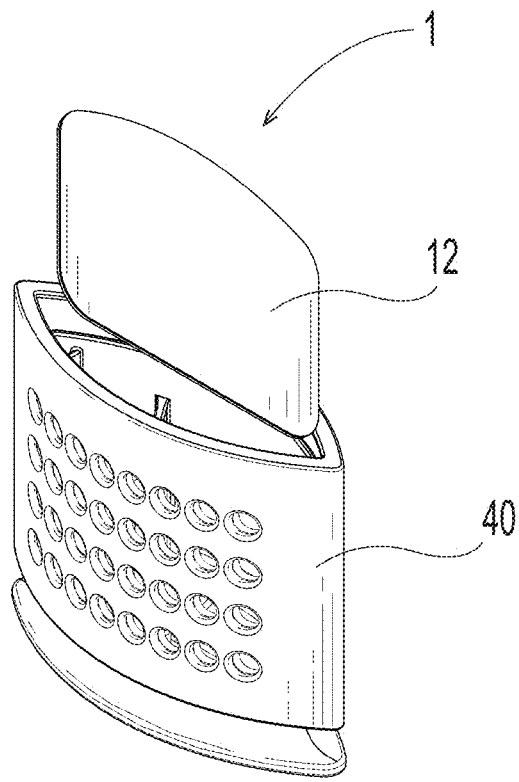
FIG. 8 is a variation of an apparatus for reducing malodor on an inanimate surface according to the present invention.

FIG. 8 shows a variation of an apparatus 1 for reducing malodor on surfaces. The apparatus 1 of FIG. 8 comprise substantially the same components of the apparatus 1 of FIG. 4 except for the housing design. Specifically, the apparatus 1 of FIG. 8 does not comprise a push button and has a different housing design from the housing 40 of the apparatus 1 in that the housing 40 of FIG. 8 is configured for releasably engaging the membrane 12 enclosing the container 10 (wherein the membrane 12 and the container 10 define a delivery engine) such that the apparatus 1 is activated upon insertion of the delivery engine.

Still further, FIGS. 9A and 9B show a variation of an apparatus 1 for reducing malodor on surfaces in a first position before activation (FIG. 9A) and a second position after activation (FIG. 9B). The apparatus 1 of FIGS. 9A and 9B differ from the apparatus 1 of FIG. 4 in that the actuator 404 is a movable clip 404 for attaching to an air vent 900 in a vehicle environment as shown in FIG. 9C. The movable clip 404 may be rotated relative to the housing 40 to move the membrane 12 and at least a portion of the rupture element 66 toward and to puncture the rupturable substrate 60 and release at least a portion of the volatile material 13 from the container 10 such that the portion of the volatile material 13 evaporates from the apparatus 1. It will be appreciated that the actuator 404 may be configured using known mechanical methods to move linearly or in a rotary motion so as to move the membrane 12 and at least a portion of the rupture element 66 toward and to puncture the rupturable substrate 60.

Demo Kit

FIG. 10 is a schematic view of a portable kit 300 for demonstrating a method of visually demonstrating the efficacy of a volatile material for reducing malodor on surfaces according to the present invention. The kit 300 may take the form of a display that can be used for sales purposes and/or for use in stores. The kit 300 comprises a first chamber 301 and a second chamber 302, each of the chambers 301 and 302 defining a closed space capable of receiving at least one inanimate surface respectively. Specifically, the first chamber 301 comprises a first inanimate surface 303, and the second chamber 302 comprises a second inanimate surface 304. Each chamber 301, 302 may comprise a length L, width W and height H and the volume of the closed space may vary depending on size of the inanimate surface placed within the closed space. The chambers 301, 302 may be configured to be separate units sized and configured for portability and ease of transportation between different locations or integral to form a single unit with separate chambers. The chambers 301, 302 may be made from or include a transparent or translucent material so as to allow users to see into the chambers 301, 302 from outside of the chambers 302, 301.

Figure 11:
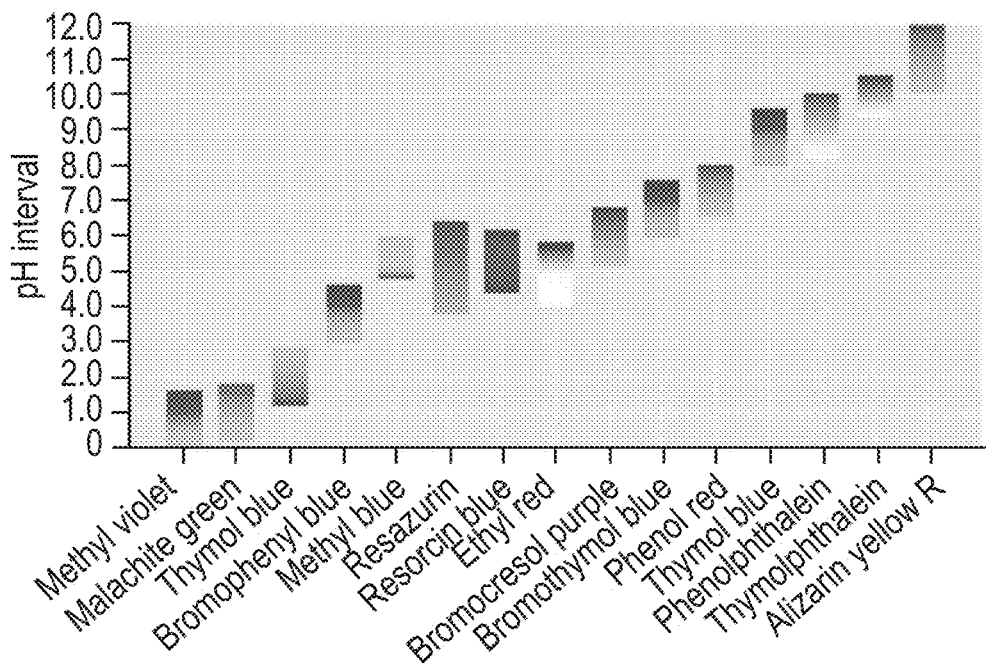
FIG. 11 is a graph showing a relationship between pH indicators and an approximate pH range over which the pH indicator change color and their change in color.

The first, second inanimate surfaces 303, 304 may be pre-treated with a pH indicator capable of exhibiting a color change upon exposure to a malodor compound. The malodor compound may belong to either acidic or base type malodor and the pH indicator may be selected accordingly to enable visual detection of the malodor compound. For example, the malodor compound may comprise a malodor substance selected from the group consisting of: ammonia, bacteria, thiols, aldehydes, amines, sulfides, fatty acids, alcohols, and mixtures thereof. The pH indicator may comprise a pH sensitive dye, such as a dye selected from the group consisting of: bromocresol green, bromocresol purple, methyl orange, methyl red, bromothymol blue, thymol blue, phenol red, neutral red, cresol red, cresolphthalein, naphtholphthalein, phenolphthalein, thymolphthalein. FIG. 11 is a graph showing a relationship between color indicators and an approximate pH range over which the pH indicator change color and their change in color. The pH indicator should be chosen such that it changes color as the amount of malodor substance changes. For example, the pH indicator may change color from a low pH color to a high pH color to indicate an increase in pH level caused by the malodor compound.

Demonstration Method

Figure 12:
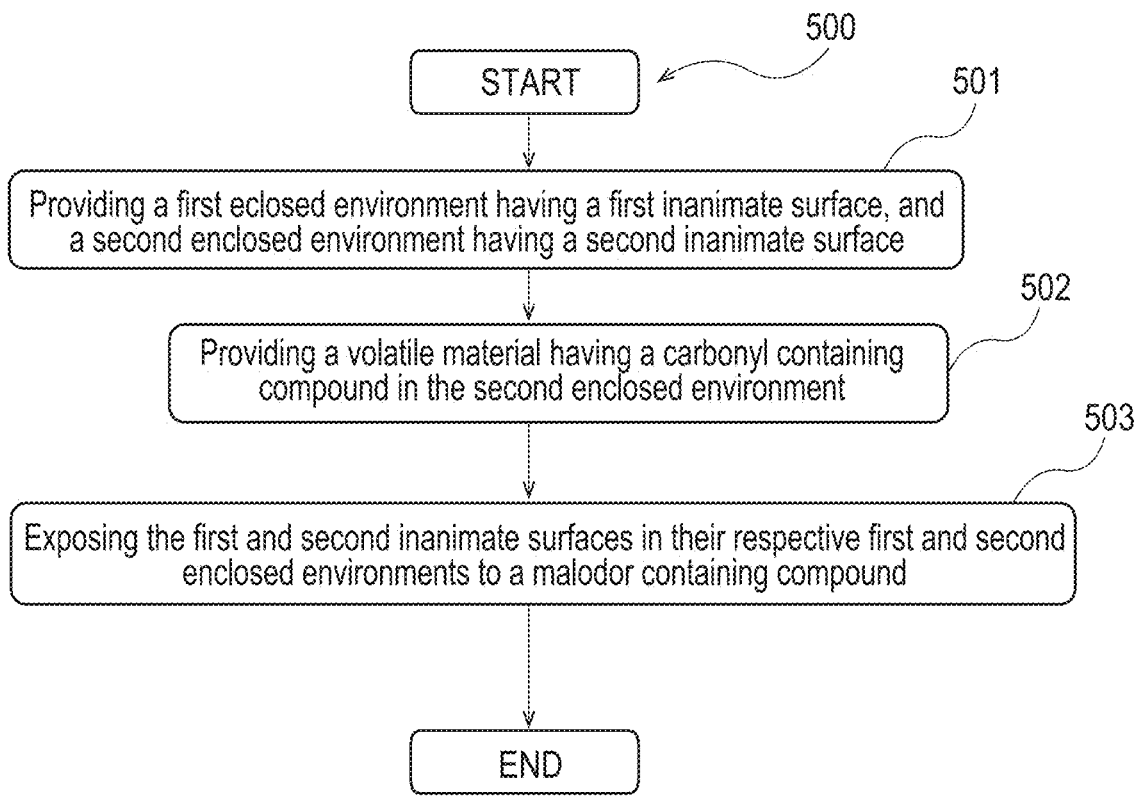
FIG. 12 is a flow chart of a method of demonstrating efficacy of a volatile material for reducing malodor on inanimate surfaces according to the present invention.

FIG. 12 is a simplified flow chart of a method 500 for demonstrating the efficacy of a volatile material for reducing malodor on an inanimate surface according to the present invention. The method 500 comprises a step 501 of providing a first chamber 301 and a second chamber 302 followed by a step 502 of providing a volatile material having a carbonyl containing compound comprised in an apparatus 1 in the second chamber 302 (shown in FIG. 13A), but not in the first chamber 301. The apparatus 1 is activated such that the volatile material 12 vaporizes and deposits a carbonyl containing compound on at least a portion of the second inanimate surface 304. In step 503 of the method 500, both the first and second odorless inanimate surfaces 303, 304 are directly exposed to a malodor introduced into the first and second chambers 301, 302. Over time, there is a change in color in the odorless first inanimate surface 303 from a first color to a second color, indicating the malodor has become attached to what was the odorless first inanimate surface 301. In contrast, there is no or only minimal change in color in the odorless second inanimate surface 302 (which had volatile material vaporized thereon) when the malodor is released into the second chamber 302. The method 500 illustrates the benefit of providing a space with a volatile material to stop transfer of malodor from a primary source (i.e. toilet bowl) to a secondary source (i.e. the wall surfaces).

Figure 13A:
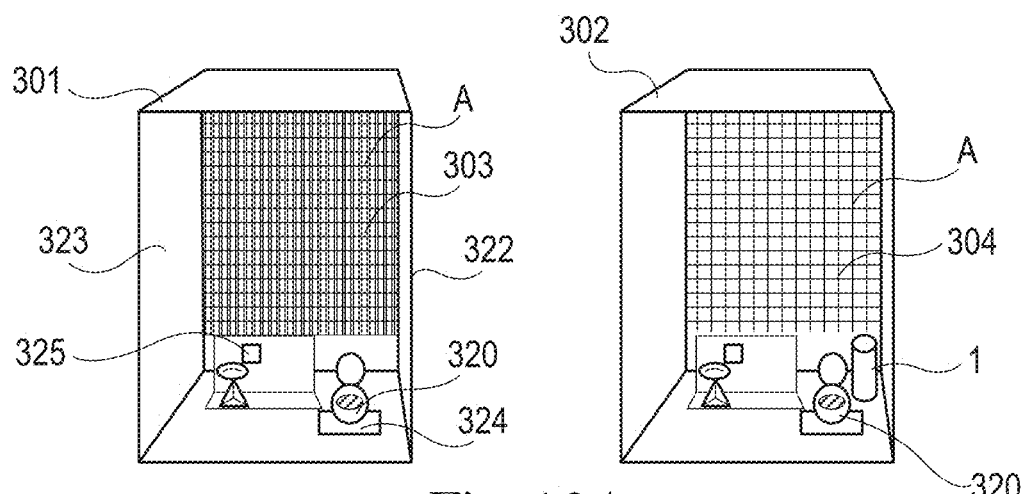
FIGS. 13A to 13C are product demonstration process diagrams for demonstrating efficacy of a volatile material for reducing malodor on inanimate surfaces according to the present invention.
Figure 13B:
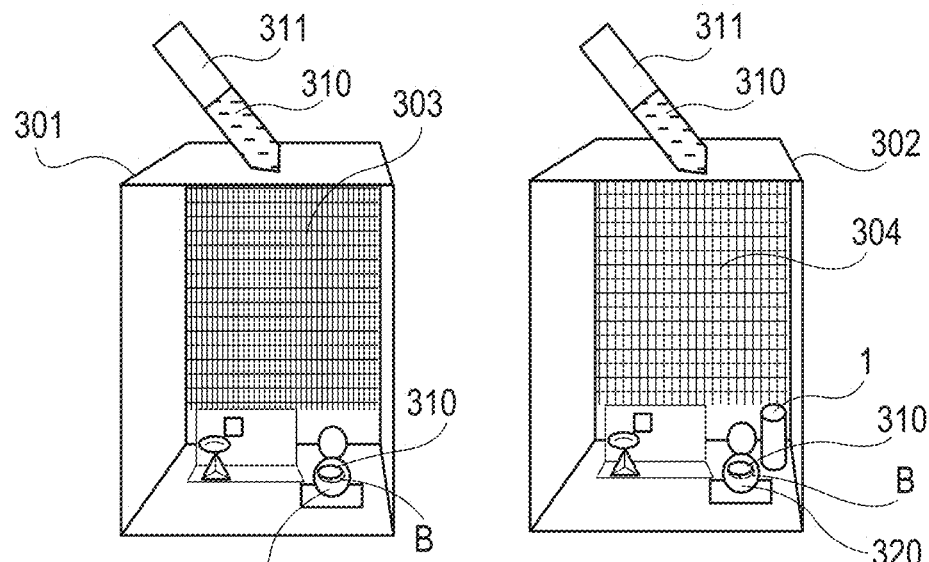
Figure 13C:
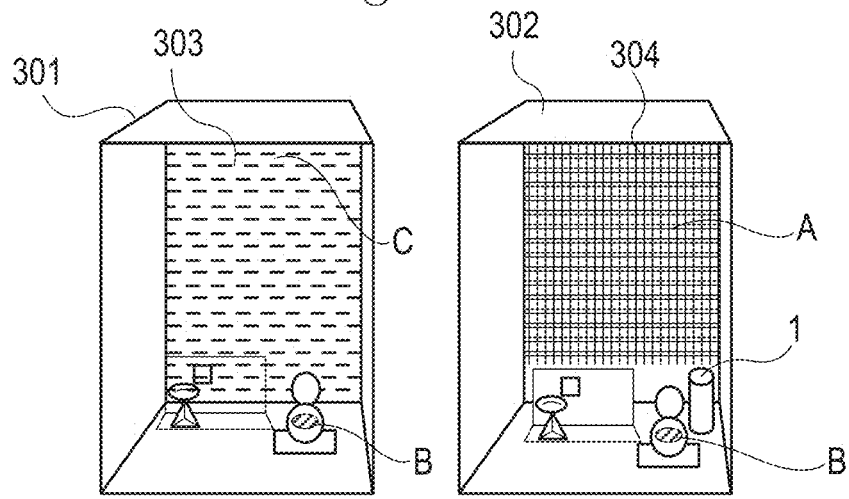

The demonstration method 500 may be also carried out as described below with reference to FIGS. 13A, 13B and 13C using the kit 300. In particular, FIGS. 13A to 13C show an example of using the kit 300 to demonstrate how malodors can attach to and remain on surfaces. For the purposes of this disclosure but without intending to limit the scope of the invention, the kit 300 may further comprise miniature customizable components (such as miniature model furniture, appliances, hardware or the like) arranged to depict a miniature model space to better illustrate to customers/consumers how the apparatus 1 works in an interior space and to demonstrate the method 500 according to the present invention. It should be appreciated that the method 500 may also be demonstrated in actual size interior spaces or spaces of any other desired scale.

In FIG. 13A, the first and second chambers 301, 302 of the kit 300 are configured to show two miniature model bathrooms (hereinafter "first and second model rooms 301, 302"). Both have a miniature toilet bowl 320 for functioning as a primary malodor source when malodor compounds are present in the miniature toilet bowl 320 and the same interior surfaces (e.g. rear walls 322 and side walls 323, rugs 324 and towels 325). FIG. 13A shows how the interior surfaces look prior to a malodor being introduced into the first and second model rooms 301, 302. The rear wall 322 of the first and second model rooms 301, 302 may comprise inanimate surfaces 303, 304 which have been treated with a pH indicator that will change color when malodor molecules are present. Prior to performing the method 500, the first, second inanimate surfaces 303, 304 should be substantially free from malodor ("odorless") and may comprise a first color A. The apparatus 1 is provided in the second model room 302 but not in the first model room 301. For the purposes of conducting the product demonstration in a short amount of time to customers and/or consumers, a predetermined amount (e.g. 0.1 to 0.3 milliliters) of the carbonyl containing compound of the volatile material 12 may be pre-deposited on the surface 304 of the second model room 302 to simulate a predetermined time of the carbonyl containing compound of the volatile material 12 comprised in the apparatus 1 (being activated) vaporizing and depositing on the surface 304 of the second model room 302. The predetermined amount of 4 to 6 milliliters is calculated based on the volume of the second model room 302 having dimensions of 30 cm H×25 cm W×20 cm L. However, it should be appreciated that the volatile material comprising the carbonyl containing compound may vaporize from the apparatus 1 (such as shown in any of FIGS. 1 to 9C) and deposit on the inanimate surface 304 of the second model room 302 to reduce malodor on surfaces (such as demonstrated in the results of Example III).

FIG. 13B is a representation of how a malodor containing compound 310 is introduced into the respective environment in the first and second model rooms 301, 302 via a dropper device 311 comprising the malodor containing compound 310. Specifically, the malodor container compound 310 is added to both model rooms 301, 302 such as in the miniature toilet bowls 320 disposed therein, and allowed to sit for a predetermined time period. The predetermined time period may vary depending on a concentration of the malodor containing compound 310 in the model rooms 302. The malodor compound may be configured so as to exhibit a second color B, such as a bright pink color (based on a pH indicator being Phenolphthalein), whereas the first color A of the inanimate surfaces 303, 304 may be a different color, for example, white.

FIG. 13C is a representation of how the first and second model rooms 301, 302 appear after the malodor containing compound has been introduced into the environment. The pink color (due to the pH indicator changing colors) on some of the surfaces shows that malodor molecules are present on the surfaces. As can be clearly seen in FIG. 13C, the surfaces of the first model room 301 without the apparatus 1 have malodor molecules thereon, whereas the surfaces of the second model room 302 (with the apparatus 1) do not indicate that malodor molecules are attached thereto. This clearly demonstrates that the carbonyl containing compound in the apparatus 1 has prevented the malodor compound 310 from being deposited on the surfaces in the model room including the apparatus and/or that the carbonyl containing compound neutralized the malodor that was deposited on the second inanimate surface 304. Either way, the amount of malodor molecules on the second surface 304 is significantly lower than those on the first surface. As such, the second surface 304 will be much less likely to act as a secondary odor source for the room.

The specific colors shown help to enable clear visualization of any transfer of the malodor compound to the first and second inanimate surfaces 303, 304. However, any colors are acceptable so long as the user can detect a difference between the colors.

FIG. 13C shows that the first inanimate surface 303 in the first model room 301, which does not include a volatile material 12 comprising the carbonyl containing compound (represented by the apparatus 1), has malodor particles on the first surface 303 reacting with the pH indicator present in the first inanimate surface 303. The first inanimate surface 303 may exhibit a color change from a first color A to a second color C wherein the second color C may correspond to the color B of the malodor compound 12. On the other hand, no or minimal color change is generated in the second inanimate surface 304 (i.e. the second inanimate surface 304 is substantially of the first color A) which demonstrates having a volatile material deposited on the second inanimate surface 304 has neutralized and reduced the malodor compound present on the second inanimate surface 304. Consequently, malodor is prevented from being released into the air from the second inanimate surface 304 and therefore malodor is not transferred to the air from the second inanimate surface 304.

A benefit of the method 500 according to the present invention is to visually demonstrate through a color change that inanimate surfaces in a space can become secondary malodor sources which absorb and re-emitting malodor hence creating a cycle of odor in a closed space such as in the house. Therefore, providing a volatile containing compound comprising a carbonyl containing compound alone or an apparatus comprising a volatile containing compound comprising a carbonyl containing compound in the closed space enables reduction of malodor on inanimate surfaces. If done over time, this method provides a passive and effective way to eliminate secondary malodor sources from enclosed spaces.

Test Methods

A. Malodor Neutralization Test Method

This test method is used to detect neutralization of malodor by a volatile material comprising a carbonyl containing compound according to the present invention deposited on at least a part of an inanimate surface comprising a permeable material. Specifically, where the carbonyl containing compound is an aldehyde containing compound such as described in Table 1, generation of a Schiff base demonstrates that the carbonyl containing compound undergoes a nucleophilic addition to neutralize the malodor.

Equipment and materials used in the experiment are listed in Table 5 below.

TABLE 5

| Equipment/Materials | |
|---|---|
| Component | Example |
| Malodor containing compound | Butylamine or Aniline |
| Malodor containing solution | Solution of: |
| | 22.2 ng of Malodor containing compound |
| | 100 μL of $3.04 \times 10^{-3}$ M standard in methanol |
| Carbonyl containing compound | 1.0 ml of (E)-hex-2-enal neat standard per Sample |
| Apparatus 1 | Aluminum dish (Quantity = 2) |
| Inanimate Surfaces | 2 cm × 2 cm square of cotton-polyester twill fabric (twelve pieces) |
| First Enclosure 71 | 1 liter glass bottle and cap (shown in FIG. 14) |
| Second Enclosure 72 | 1 liter glass bottle and cap (shown in FIG. 14) |
| Gas Chromatography Mass Spectography (GCMS) Equipment | GCMS Agilent Technologies 7890B GC System with 5977B HES-MSD |
| Software | Autosampler |
| | GERSTEL-MultiPurposeSampler MPS 2XL-XT, Version Headspace + Liquid injection, including DynamicHeadSpace DHS for GERSTEL-MPS-2/TDU The autosampler is used with the GCMS to automate the analysis. |
| | Software |
| | MassHunter B07.05 |
| | GERSTELMaestro Software 1.4.40.1 |

Figure 14:
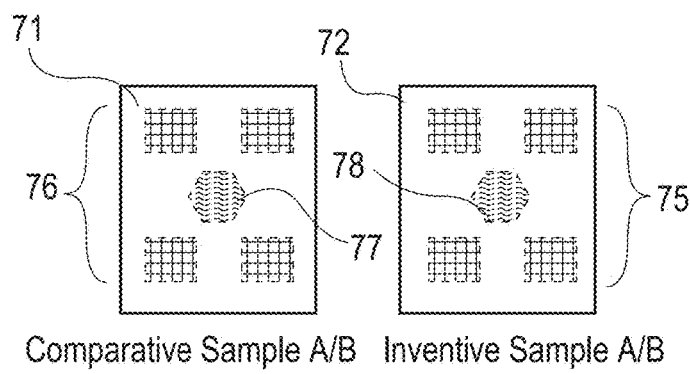
FIG. 14 is a schematic view of sample placement according to the Malodor Neutralization Test Method.

The test method is performed in a set up according to FIG. 14 and at an average temperature of 23° C.+/−0.1° C., and an average % relative humidity of 45%+/−0.5%. The steps for performing the test include:

Step 1: Treating four inanimate surfaces by depositing 22.2 ng of the malodor containing solution of Table 5 on each of the inanimate surfaces to form four malodor containing inanimate surfaces 75. Four inanimate surfaces are untreated ("odorless inanimate surfaces 76").

Step 2: Four odorless inanimate surfaces are placed in first enclosure 72 to define Comparative Sample A/Comparative Sample B. Another different set of four malodor containing inanimate surfaces is placed in second enclosure 72 to define Inventive Sample A/Inventive Sample B.

Step 3: 1.0 ml of the carbonyl containing compound is pipetted into each of first and second receptacles 77, 78. The first receptacle 77 is placed in first enclosure 71 while the other aluminum dish is placed in third enclosure 73.

Step 4: The first and second enclosures 71, 72 are enclosed by fitting a lid over each of the enclosures 71, 72 and allow equilibration for a time period of 30 minutes.

Step 5: All the inanimate surfaces of the Comparative Sample A/Comparative Sample B and Inventive Sample A/Inventive Sample B are removed from the respective enclosures and analysed using the GCMS equipment and software described in the above to determine:

Malodor neutralization according to the present invention (Inventive Sample A/Inventive Sample B)

Vaporisation and Deposition of carbonyl containing compound on inanimate surface (Comparative Sample A/Comparative Sample B)

B. Malodor Performance Test Method

This test method is used to evaluate the effectiveness of a method in reducing or removing malodor from inanimate surfaces and/or an environment. Equipment and materials used in the experiment are listed in Table 6 below.

TABLE 6

| Component | Example |
| --- | --- |
| Malodor containing compound (Primary Malodor Source 150) | Malodor Containing compound - Fish (1 gram) is used as an example of an amine-containing compound for tests done on fabric Synthetic Urine comprising urea (1 to 1.5 grams) is used as an example of an amine-containing compound for tests done on drywall and wall paper. |
| Inanimate Surface comprising Permeable Material (Inanimate Surface 151) | Twenty pieces of 20 cm × 20 cm square of cotton-polyester twill fabric/Drywall (Knauf standard board W111-1)/Wall paper (PVC-polyester wallpaper with acrylic adhesive paper KW-54 by Asahi) |
| Chambers 171, 172, 173, 174, 175, 176, 177, 178 | Supplier: ETS (Electro-Tech Systems) 3101 Mt. Carmel Avenue, Glenside, PA 19038 Tel 215-887-2196\|Fax 215-887-0131 Chamber Specifications: Model 5518-8039 (Custom Built) Dimensions 39.25" W × 25" D × 21.5"H Volume 12.2 cu. ft. (.34 cu. meters) Access Openings Large Front: 32" × 14" Small Front: 14" × 4" Side: 14" × 4" |

Figure 15:
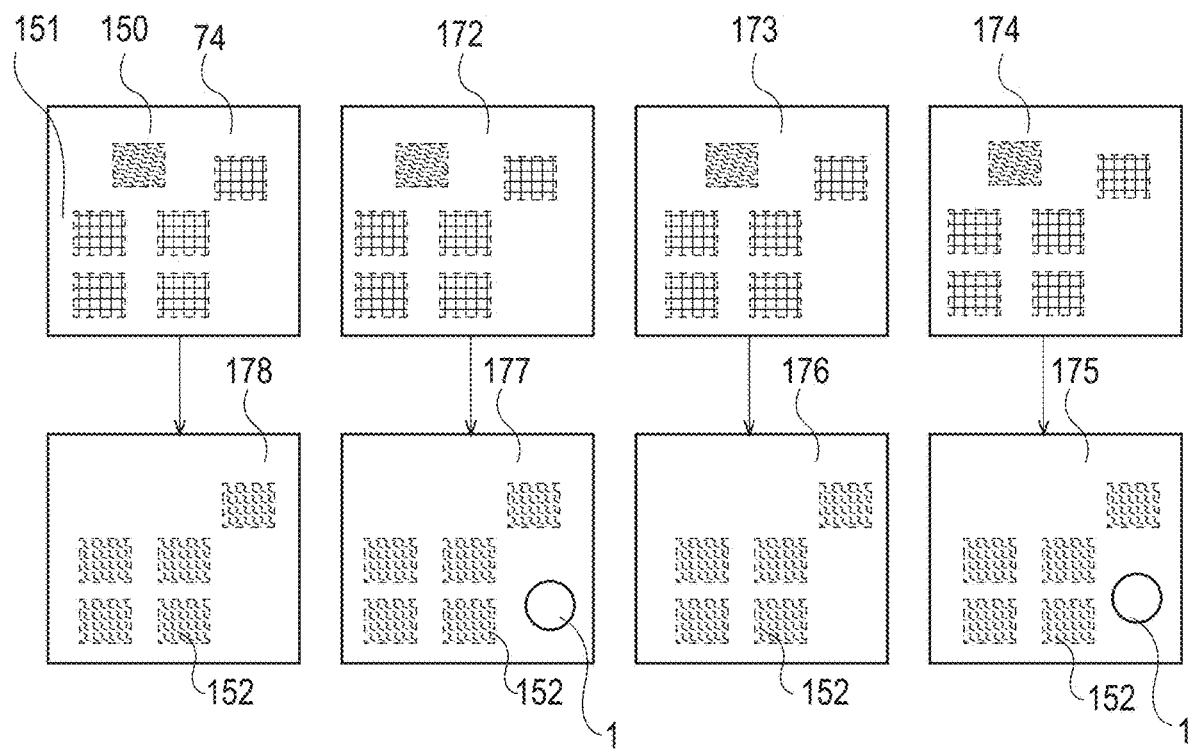
FIG. 15 is a schematic view of sample placement according to Malodor Performance Test Method.

The test method is performed in a set up according to FIG. 15 and at an average temperature of 22° C.+/−0.1° C., and an average % relative humidity of 60%+/−5%. The steps for performing the test include:

Step 1: A set of five inanimate surfaces 151 are placed in each of Chambers 171, 172, 173, 174 comprising the primary malodor sources 150 for 30 minutes to expose the five inanimate surfaces to the primary malodor sources so as to form malodor containing inanimate surfaces (hereinafter "secondary malodor sources 152").

Step 2: An apparatus 1 comprising a volatile material having a carbonyl containing compound according to the present invention is placed in each of Chambers 175 and 177.

Step 3: The inanimate surfaces (also known as secondary malodor sources obtained in Step 1) are transferred from Chambers 171, 172, 173, 174 and are placed in Chambers 175, 176, 177, 178 for 45 minutes.

Step 4: The inanimate surfaces from Chambers 175, 176, 177 and 178 are evaluated by panelists, whereby each panelist evaluates one inanimate surface from any one of the Chambers 175, 176, 177, 178 and grade the inanimate surfaces for malodor and/or perfume odour according to intensity ratings are based on odor grading using the scale shown in Table 7 below. The air in the Chambers 175, 176, 177, 178 may also be graded for malodor and/or perfume odour. This may be helpful in evaluation of surfaces which are not practical for removal (such as drywall). However, it will be appreciated that the odor grade value of the inanimate surface may be reduced accordingly as it is believed that the inanimate surface comprising the malodor functions as a secondary malodor source that contributes to the malodor in the air.

TABLE 7

| Odor Evaluation Scale | |
|---|---|
| Score | Description corresponding to Score |
| 0 | No odor present |
| 10 | Very slight odor "I think there is an odor present" |
| 20 | Slight odor "I detect something but cannot identify specific odor" |
| 25 | Slight Odor |
| 50 | Moderate |
| 75 | Strong odor |
| 100 | Extremely strong odor |

C. Visual Demonstration Test Method

This test method is used to show visually how malodor is reduced by providing an apparatus comprising a volatile carbonyl containing compound according to the present invention in an enclosed space. Equipment and materials used in the experiment are listed in Table 8 below.

TABLE 8

| Component | Example |
|---|---|
| Malodor containing compound (Primary Malodor Source) | Ammonia (Cat no. 01266-00, Caca-Reagent 28%) is used as an example of an amine-containing compound |
| Inanimate Surface comprising Permeable Material and pH indicator | Phenolphthalein paper (AGG#PRE-235-24-8x10) |
| First and Second Chambers | Supplier: ETS (Electro-Tech Systems) |
| | 3101 Mt. Carmel Avenue, Glenside, PA 19038 |
| | Tel 215-887-2196\|Fax 215-887-0131 |
| | Chamber Specifications: |
| | Model 5518-8039 (Custom Built) |
| | Dimensions 39.25" W x 25" D x 21.5"H |
| | Volume 12.2 cu. ft. (.34 cu. meters) |
| | Access Openings Large Front: 32" x 14" |
| | Small Front: 14" x 4" |
| | Side: 14" x 4" |
| Dropper for adding malodor containing compound into chambers | Fisher 1 ml Dropper |
| Receptacle for Receiving Malodor containing compound | Plastic Petri Dish (Supplier: Fisher) |

The test method is performed at an average temperature of 22° C.+/−0.1° C., and an average % relative humidity of 60%+/−5%. The steps for performing the test include:

Step 1: An inanimate surface treated with a pH indicator is placed in the centre of a back wall of each of the first and second chambers.

Step 2: A receptacle for receiving a malodor containing compound is placed in each chamber at a distance of 20 cm from the inanimate surface.

Step 3: An apparatus comprising a carbonyl containing compound according to the present invention is activated and placed in the first chamber and positioned between the receptacle and the inanimate surface ("Test Chamber"). The second chamber does not have the apparatus or a carbonyl containing compound ("Control Chamber").

Step 4: The Test and Control Chambers are closed and allowed to sit for a time period of 8 hours.

Step 5: At the end of the time period of 8 hours, the Test and Control Chambers are opened and 1 to 1.5 ml of the malodor containing compound is added to the receptacle of each of the Chambers. The Chambers are closed.

Step 6: After a time period of 10 minutes, the inanimate surfaces in the Chambers are observed for a color change.

The following examples further illustrate the invention, but are not intended to be limiting thereof.

EXAMPLES

Example I

The following Samples in Table 9 are evaluated according to the Malodor Neutralization Test Method described hereinbefore under Test Methods.

TABLE 9

| Ingredients | Comparative Sample A, Comparative Sample B | Inventive Sample A, Inventive Sample B |
|---|---|---|
| Carbonyl Containing Compound | 1.0 ml of (E)-hex-2-enal | 1.0 ml of (E)-hex-2-enal |
| Apparatus for receiving the carbonyl containing compound | Dish made of Aluminum foil | Dish made of Aluminum foil |

Figure 16:
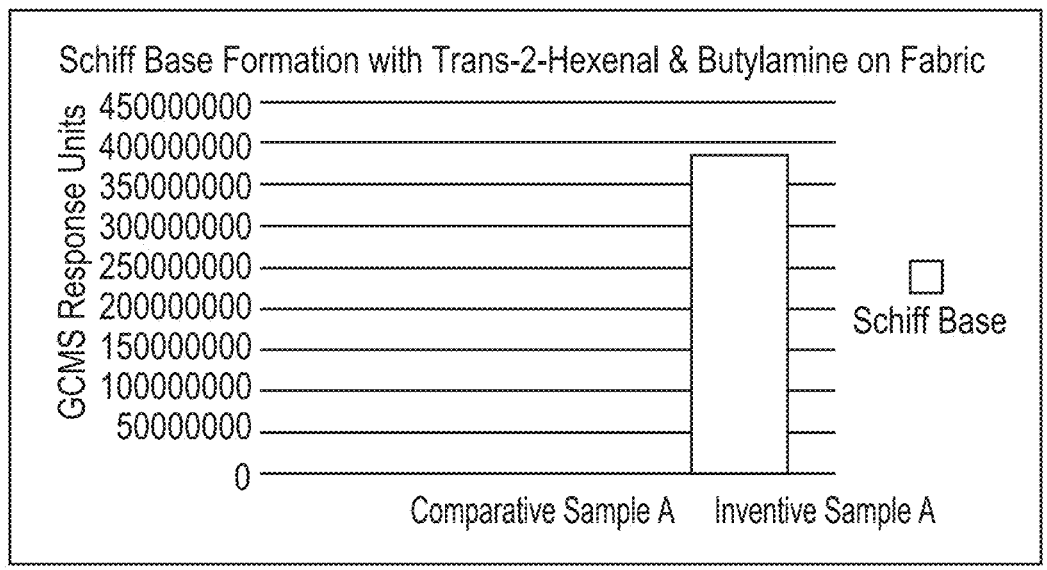
FIG. 16 is a graph plotting the gas chromatography mass spectrography (GCMS) response units of Comparative SampleA and Inventive Sample A.
Figure 17:
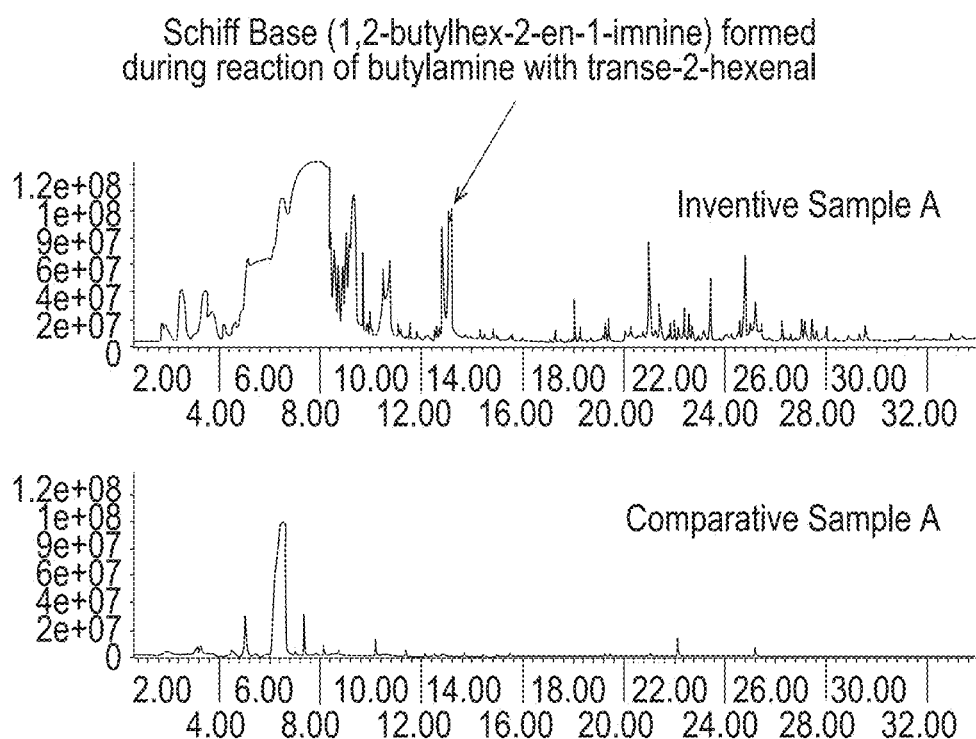
FIG. 17 are chromatographs of Comparative Sample A and Inventive Sample A.

Comparative Sample A and Inventive Sample A are allowed to stabilize for a time period of 30 minutes. Each of the inanimate surfaces in the abovementioned samples were retrieved after the time period for analysis in GCMS (Gas Chromatography Mass Spectrography). Referring to FIGS. 16 and 17, the GCMS results (with reference to FIG. 16) show that a Schiff base (1,2-butylhex-2-en-1-imnine) is observed in Inventive Sample A which demonstrates that there is neutralization of the malodor containing compound (butylamine) by the carbonyl containing compound (trans-2-hexenal). Specifically, minimal or no butylamine is detected on Inventive Sample A. Further, the results also show that the carbonyl containing compound is deposited on the inanimate surface of Comparative Sample A which demonstrates that the carbonyl containing compound according to the present invention, i.e. Trans-2-Hexenal is capable of vaporizing and depositing on the inanimate surface.

Comparative Sample B and Inventive Sample B are allowed to stabilize for a time period of 30 minutes. Each of the inanimate surfaces in the abovementioned samples were retrieved after the time period for analysis in GCMS (Gas Chromatography Mass Spectrography). Referring to FIGS. 18 and 19, the GCMS results (with reference to FIG. 18) show that a Schiff base (1,2-phenylhex-2-en-1-imnine) is observed in Inventive Sample B which demonstrates that there is neutralization of the malodor containing compound (aniline) by the carbonyl containing compound ((E)-hex-2-enal). Specifically, minimal or no aniline is detected on Inventive Sample B.

Example II

The following samples in Table 10 are evaluated according to the Malodor Performance Test Method described hereinbefore under Test Methods. Accords C, D and E used to prepare the samples are detailed in Tables 11, 12 and 13 below. The results show that an apparatus having volatile material comprising carbonyl containing compounds capable of vaporizing and depositing on inanimate surfaces exhibit improved performance in reducing malodor on inanimate surfaces and/or in the air of an enclosed space.

TABLE 10

| Parts/Parameters | Inventive Sample C | Inventive Sample D | Inventive Sample E |
|---|---|---|---|
| Composition | 6 ml | 6 ml | 6 ml |
| Volatile Material | 4% by weight of the Composition | 100% by weight of the Composition | 100% by weight of the Composition |
| Carbonyl Containing Compound(s) | 100% by weight of the volatile material of Accord C of Table 11 | 4% by weight of the volatile material of Accord D of Table 12 | 4% by weight of the volatile material of Accord E of Table 13 |
| Other Common Perfume Raw Materials including esters, ethers, alcohols but not including the abovementioned carbonyl containing compound(s) | None | 96% by weight of the volatile material | 96% by weight of the volatile material |
| Solvent | Dimethyl glutarate in an amount of 96% by weight of the Composition | — | — |
| Apparatus for receiving the volatile material | As shown in FIG. 4 | As shown in FIG. 4 | As shown in FIG. 4 |

TABLE 11

Accord C

| CAS No. | Material Name | Weight % by weight of the Volatile Material (Inventive Sample C of Table 10) | VP (torr) @ 25° C. |
|---|---|---|---|
| 6728-26-3 | (E)-hex-2-enal | 3.10 | 10.66 |
| 1335-66-6 | 2,4,6-trimethylcyclohex-3-ene-1-carbaldehyde; 3,5,6-trimethylcyclohex-3-ene-1-carbaldehyde | 6.20 | 2.64 |
| 124-13-0 | octanal | 9.30 | 1.14 |
| 68039-49-6 | 2,4-dimethylcyclohex-3-ene-1-carbaldehyde | 15.49 | 0.73 |
| 106-72-9 | 2,6-dimethylhept-5-enal | 15.49 | 0.48 |
| 2277-19-2 | (Z)-non-6-enal | 0.22 | 0.22 |
| 557-48-2 | (2E,6Z)-nona-2,6-dienal | 0.62 | 0.18 |
| 100-52-7 | benzaldehyde | 9.30 | 0.13 |
| 5392-40-5 | (2E)-3,7-dimethylocta-2,6-dienal | 9.30 | 0.13 |
| 112-31-2 | decanal | 15.49 | 0.12 |
| 30772-79-3 | 4,7-Methanoindan-1-carboxaldehyde | 15.49 | 0.05 |
| | Total by weight of the Volatile Material | 100% | |

TABLE 12

Accord D

| CAS No. | Material Name | Weight % by weight of the Volatile Material (Inventive Sample D of Table 10) | VP (torr) @ 25° C. |
|---|---|---|---|
| 68039-49-6 | 2,4-dimethylcyclohex-3-ene-1-carbaldehyde | 1.8 | 0.73 |
| 106-72-9 | 2,6-dimethylhept-5-enal | 0.4 | 0.48 |
| 33885-52-8 | 3-(6,6-dimethyl-4-bicyclo[3.1.1]hept-3-enyl)-2,2-dimethylpropanal | 1.8 | 0.028 |
| | Total by weight of the Volatile Material | 4 | |

TABLE 13

Accord E

| CAS No. | Material Name | Weight % by weight of the Volatile Material (Inventive Sample D of Table 10) | VP (torr) @ 25° C. |
|---|---|---|---|
| 68039-49-6 | 2,4-dimethylcyclohex-3-ene-1-carbaldehyde | 0.44 | 0.73 |
| 65405-70-1 | (E)-dec-4-enal | 0.26 | 0.35 |
| 557-48-2 | (2E,6Z)-nona-2,6-dienal | 0.03 | 0.18 |
| 62439-41-2 | 6-methoxy-2,6-dimethylheptanal | 0.17 | 0.130 |
| 112-31-2 | Decanal | 1.31 | 0.12 |
| 33885-52-8 | 3-(6,6-dimethyl-4-bicyclo[3.1.1]hept-3-enyl)-2,2-dimethylpropanal | 1.80 | 0.028 |
| | Total by weight of the Volatile Material | 4 | |

Tables 14, 15 and 16 shows average odor values provided by panelists based on the odor grading (as shown in Table 7) when Inventive Samples C, D and E are tested on inanimate surfaces including fabric, drywall and wall paper. Specifically, the results show that malodor is reduced on the inanimate surfaces and in the air of the environment when an apparatus according to the present invention is provided in the environment.

TABLE 14

Odor Results - Inventive Sample C

| Average Odor Value according to Scale as shown in Table 7 | TEST SURFACE: FABRIC | | |
|---|---|---|---|
| | Chambers 176, 178 each is a Control Sample with Test Surface Only | Chambers 175, 177, each having Inventive Sample C | Delta Odor value |
| Average Odor Value of Test Surface | 32 | 21 | 12 |
| Average Odor Value of Air | 37 | 19 | 18 |

TABLE 15

Odor Results - Inventive Sample D

| Average Odor Value according to Scale as shown in Table 7 | TEST SURFACE: FABRIC | | |
|---|---|---|---|
| | Chambers 176, 178 each is a Control Sample with Test Surface Only | Chambers 175, 177, each having Inventive Sample D | Delta Odor value |
| Average Odor Value of Test Surface | 38 | 18 | 20 |
| Average Odor Value of Air | 41 | 15 | 26 |

TABLE 16

Odor Results - Inventive Sample E

| Average Odor Value according to Scale as shown in Table 7 | TEST SURFACE: FABRIC | | |
|---|---|---|---|
| | Chambers 176, 178, each is a Control Sample with Test Surface only | Chambers 175, 177, each having Inventive Sample E | Delta Odor value |
| Average Odor Value of Test Surface | 39 | 20 | 19 |
| Average Odor Value of Air | 39 | 15 | 24 |

The results in Tables 14, 15 and 16 show that the volatile material according to the present invention does not require perfume raw materials to reduce malodor. Even though a perfume raw material is added such as for Inventive Samples D and E, the scores are improved from 21 to 18 as shown for Inventive Sample D relative to Inventive Sample C and from 21 to 20 as shown for Inventive Sample E relative to Inventive Sample C, the differences in the scores are minimal. This demonstrates that having the volatile material substantially free of perfume raw material according to the present invention is effective in reducing malodor on the inanimate surface thereby eliminating secondary malodor sources as shown in the reduced odor values of air in the above tables. Inventive Samples D and E are also evaluated for effectiveness in malodor reduction on wallpaper and drywall (specified below) according to the Malodor Performance Test Method described hereinbefore under Test Methods. The results are shown below.

TABLE 17

Odor Results - Inventive Sample D

TEST SURFACE: Wall Paper PVC-polyester wallpaper with acrylic adhesive grade KW54 by Asahi

| Average Odor Value according to Scale as shown in Table 7 | Chambers 176, 178 each is a Control Sample with Test Surface only | Chambers 175, 177, each having Inventive Sample D | Delta Odor value |
|---|---|---|---|
| Average Odor Value of Test Surface | 31 | 18 | 13 |
| Average Odor Value of Air | 42 | 25 | 18 |

TABLE 18

Odor Results - Inventive Sample E

TEST SURFACE: Drywall (Supplier name: Knauf, Grade: Knauf standard board W111-1

| Average Odor Value according to Scale as shown in Table 7 | Chambers 176, 178, each is a Control Sample with Test Surface only | Chambers 175, 177, each having Inventive Sample E | Delta Odor value |
|---|---|---|---|
| Average Odor Value of Air | 45 | 12 | 33 |

Table 18 does not include odor value result of the surface when evaluated with Inventive Sample E as it would not be practical to extract the drywall for odor evaluation by panelists. However, as shown in the results for Inventive Sample E (in Table 16), it is anticipated that if the odor value of air is reduced, the odor value of the surface disposed in the same space should also be reduced.

Example III

The following sample (Inventive Sample F) in Table 19 provided in an apparatus such as shown in FIG. 5 and is evaluated according to the Malodor Performance Test Method described hereinbefore under Test Methods. The results show that an apparatus having volatile material comprising carbonyl containing compounds capable of vaporizing and depositing on inanimate surfaces exhibit improved performance in reducing malodor on inanimate surfaces.

TABLE 19

| Inventive Sample F | |
|---|---|
| Composition | 6.5 ml |
| Volatile Material | 100% by weight of the Composition |
| Other Common Perfume Raw Materials including esters, ethers, alcohols but not including the abovementioned carbonyl containing compound(s) | 85% by weight of the Volatile Material |
| Mixture of Carbonyl Containing Compounds as listed below | 15% by weight of the Volatile Material |

| CAS No. | Material Name | VP (torr) @ 25° C. |
|---|---|---|
| 6728-26-3 | (E)-hex-2-enal | 10.66 |
| 1335-66-6 | 2,4,6-trimethylcyclohex-3-ene-1-carbaldehyde; 3,5,6-trimethylcyclohex-3-ene-1-carbaldehyde | 2.64 |

TABLE 19-continued

Inventive Sample F

| 124-13-0 | octanal | 1.14 |
| 68039-49-6 | 2,4-dimethylcyclohex-3-ene-1-carbaldehyde | 0.73 |
| 106-72-9 | 2,6-dimethylhept-5-enal | 0.48 |
| 2277-19-2 | (Z)-non-6-enal | 0.22 |
| 557-48-2 | (2E,6Z)-nona-2,6-dienal | 0.18 |
| 100-52-7 | benzaldehyde | 0.13 |
| 5392-40-5 | (2E)-3,7-dimethylocta-2,6-dienal | 0.13 |
| 112-31-2 | decanal | 0.12 |
| 30772-79-3 | 4,7-Methanoindan-1-carboxaldehyde | 0.05 |

Based on the observation after performing the test method, there is a color change in the inanimate surface in the Control Chamber without the apparatus whereas there is no color change in the inanimate surface in the Test Chamber. This shows that the apparatus 1 comprising Inventive Sample F enables compounds in the Inventive Sample F to vaporize and deposit on the surface. The compounds deposited on the inanimate surface in the Test Chamber neutralizes the malodor containing compound when the malodor containing compound comes into contact with the inanimate surface through vaporization of the malodor containing compound. This demonstrates that having the volatile material comprised in the apparatus according to the present invention is effective in reducing malodor on the inanimate surface thereby eliminating secondary malodor sources.

An example is shown below:

A. A method of reducing malodor on surfaces, the method comprising the steps of:
a) providing an apparatus in an environment including a surface comprising a permeable material having disposed thereon a malodor containing compound selected from the group consisting of: amine-containing compound and thiol-containing compound, wherein the apparatus includes a volatile material having a volatile carbonyl containing compound having a vapor pressure of at least 0.025 torr at 25 degrees Celsius; and
b) exposing the volatile material to the environment such that the volatile carbonyl containing compound vaporises and deposits on at least a portion of the surface; wherein the carbonyl containing compound undergoes a nucleophilic addition in the presence of the malodor containing compound.

B. The method according to A, further comprising a step (c) of neutralizing the malodor containing compound by a reaction product produced in step (b), thereby reducing the malodor on the surface.

C. The method according to A, wherein the step of providing an apparatus comprises providing a reservoir for the volatile material, the reservoir including an opening and a membrane sealably covering the opening of the reservoir, wherein the membrane comprises a first surface in fluid contact with the volatile material and a second surface facing the environment and away from the volatile material.

D. The method according to C, wherein the step of exposing the volatile material to the environment comprises wetting the membrane.

E. The method according to any one of A, B, C or D, wherein the vapor pressure of the volatile carbonyl containing compound is less than or equal to 30 torr at 25 degrees Celsius.

F. The method according to any one of A, B, C, D, E or F wherein the volatile carbonyl containing compound is selected from the group consisting of: volatile aldehydes, ketones, and mixtures thereof.

G. The method according to F, wherein the volatile carbonyl containing compound comprises at least one volatile aldehyde selected from the group consisting of: (E)-3-phenylprop-2-enal, benzaldehyde, 4-propan-2-ylbenzaldehyde, 4-methoxybenzaldehyde, (2E,6Z)-nona-2,6-dienal, (E)-hex-2-enal, (2E,6Z)-dodeca-2,6-dienal, non-2-enal, 2,4,6-trimethylcyclohex-3-ene-1-carbaldehyde; 3,5,6-trimethylcyclohex-3-ene-1-carbaldehyde, 3-(6,6-dimethyl-4-bicyclo[3.1.1]hept-3-enyl)-2,2-dimethylpropanal, nonanal, (E)-dec-4-enal, 2,6-dimethylhept-5-enal, (Z)-non-6-enal, 7-methoxy-3,7-dimethyloctanal, 3-(4-methylcyclohex-3-en-1-yl)butanal, 3,7-dimethyloct-6-enal, 2-methyldecanal, 2,4-dimethylcyclohex-3-ene-1-carbaldehyde, undec-10-enal, 4,8-dimethyldeca-4,9-dienal, octanal, undecanal, decanal, undec-9-enal, 6-methoxy-2,6-dimethylheptanal, 3-(6,6-dimethyl-4-bicyclo[3.1.1]hept-3-enyl)propanal, 4,7-Methanoindan-1-carboxaldehyde and mixtures thereof.

H. The method according to F, wherein the volatile carbonyl containing compound comprises at least one ketone selected from the group consisting of: 2,6,6-trimethylcyclohex-2-ene-1,4-dione, 4,7,7-trimethylbicyclo[2.2.1]heptane-2,3-dione, 1-phenylethanone, pentane-2,3-dione, 4-methoxy-2,5-dimethylfuran-3-one, 4-hydroxy-2,5-dimethylfuran-3-one, (1S,5S)-2,6,6-trimethylbicyclo [3.1.1]hept-2-en-4-one, (1R,5R)-2,6,6-trimethylbicyclo[3.1.1]hept-2-en-4-one, 3,5,5-trimethylcyclohex-2-en-1-one, 3-methylcyclopent-2-en-1-one, (5S)-2-methyl-5-prop-1-en-2-ylcyclohex-2-en-1-one, (5R)-2-methyl-5-prop-1-en-2-ylcyclohex-2-en-1-one, 4-methylpent-3-en-2-one, 2-methyl-5-prop-1-en-2-ylcyclohex-2-en-1-one, 1-(1H-pyrrol-2-yl)ethenone, (5R)-5-methyl-2-propan-2-ylidenecyclohexan-1-one, 4-methylpent-3-en-2-one, 2-methyl-5-prop-1-en-2-ylcyclohex-2-en-1-one, 1-(1H-pyrrol-2-yl)ethenone, (5R)-5-methyl-2-propan-2-ylidenecyclohexan-1-one, 4-phenylbutan-2-one, 3-methylbutyl 3-oxobutanoate, 3-hydroxybutan-2-one, (Z)-3,4,5,6,6-pentamethylhept-3-en-2-one, 3-oxobutan-2-yl acetate, methyl 3-oxobutanoate, ethyl 3-oxobutanoate, (2R,5R)-2-methyl-5-prop-1-en-2-ylcyclohexan-1-one, 2-methyl-5-prop-1-en-2-ylcyclohexan-1-one, (2S,5S)-2-methyl-5-prop-1-en-2-ylcyclohexan-1-one, 2-ethyl-4,4-dimethylcyclohexan-1-one, 1-(3,3-dimethylcyclohexyl)ethenone, (2S,5S)-5-methyl-2-propan-2-ylcyclohexan-1-one, (2S,5R)-5-methyl-2-propan-2-ylcyclohexan-1-one, 2,2,5-trimethyl-5-pentylcyclopentan-1-one, 3,3,5-trimethylcyclohexan-1-one, 2-cyclopentylcyclopentan-1-one, (1S,4R,5R)-4-methyl-1-propan-2-ylbicyclo[3.1.0]hexan-3-one, 4-(2-methylbutan-2-yl)cyclohexan-1-one, 4,7,7-trimethylbicyclo[2.2.1]heptan-3-one, 6-methylhept-5-en-2-one, octan-2-one, (1S,4R)-2,2,4-trimethylbicyclo[2.2.1]heptan-3-one, heptan-2-one, 2,2,4-trimethylbicyclo[2.2.1]heptan-3-one, 5-methylheptan-3-one, octan-3-one, and mixtures thereof.

I. The method according to any one of A, B, C, D, E, F, G, or H wherein the volatile carbonyl containing compound is in an amount of greater than or equal to 0.01% to less than or equal to 25%, by weight of the volatile material.

J. The method according to any one of A, B, C, D, E, F, G, H, or I, wherein the permeable material is selected from the group consisting of: fabrics, drywall, wovens, paper, natural polymers, synthetic polymers and inorganic materials and mixtures thereof.

K. The method according to any one of A, B, C, D, E, F, G, H, I or J, wherein the volatile material comprises a volatile aldehyde mixture selected from the group consisting of Accord A, Accord B and mixtures thereof.

L. An apparatus for reducing malodor on surfaces, the apparatus comprising: a housing comprising a rear frame having one or more apertures spaced from the frame opening; an actuator movable relative to the rear frame;
a container disposed within the housing, the container including a reservoir containing a volatile material having a carbonyl containing compound having a vapor pressure of greater than or equal to 0.025 torr at 25 degrees Celsius, an opening, a rupturable substrate attached to and covering the opening and a rupture element aligned with the actuator to;
upon activation of the actuator, the rupture element ruptures the rupturable substrate, whereby at least a part of the volatile material including the volatile carbonyl containing compound vaporises and exits the apparatus to enter the environment;
wherein the carbonyl containing compound of the volatile material can undergo a nucleophilic addition in the presence of a malodor containing compound selected from the group consisting of: amine-containing compound and thiol-containing compound.

M. The apparatus according to L, wherein the actuator is a push button movably disposed within a frame opening of the rear frame.

N. The apparatus according to M, including a membrane disposed adjacent the rupturable substrate and aligned with the push button.

O. The apparatus according to any one of L, M or N, wherein the volatile carbonyl containing compound is selected from the group consisting of: volatile aldehydes, ketones and mixtures thereof.

P. The apparatus according to O, wherein volatile carbonyl containing compound comprises at least one volatile aldehyde selected from the group consisting of: (E)-3-phenylprop-2-enal, benzaldehyde, 4-propan-2-ylbenzaldehyde, 4-methoxybenzaldehyde, (2E,6Z)-nona-2,6-dienal, (E)-hex-2-enal, (2E,6Z)-dodeca-2,6-dienal, non-2-enal, 2,4,6-trimethylcyclohex-3-ene-1-carbaldehyde; 3,5,6-trimethylcyclohex-3-ene-1-carbaldehyde, 3-(6,6-dimethyl-4-bicyclo[3.1.1]hept-3-enyl)-2,2-dimethylpropanal, nonanal, (E)-dec-4-enal, 2,6-dimethylhept-5-enal, (Z)-non-6-enal, 7-methoxy-3,7-dimethyloctanal, 3-(4-methylcyclohex-3-en-1-yl)butanal, 3,7-dimethyloct-6-enal, 2-methyldecanal, 2,4-dimethylcyclohex-3-ene-1-carbaldehyde, undec-10-enal, 4,8-dimethyldeca-4,9-dienal, octanal, undecanal, decanal, undec-9-enal, 6-methoxy-2,6-dimethylheptanal, 3-(6,6-dimethyl-4-bicyclo[3.1.1]hept-3-enyl)propanal, 4,7-Methanoindan-1-carboxaldehyde and mixtures thereof.

Q. The apparatus according to O, wherein the volatile carbonyl containing compound comprises at least one ketone selected from the group consisting of: 2,6,6-trimethylcyclohex-2-ene-1,4-dione, 4,7,7-trimethylbicyclo[2.2.1]heptane-2,3-dione, 1-phenylethanone, pentane-2,3-dione, 4-methoxy-2,5-dimethylfuran-3-one, 4-hydroxy-2,5-dimethylfuran-3-one, (1S,5S)-2,6,6-trimethylbicyclo[3.1.1]hept-2-en-4-one, (1R,5R)-2,6,6-trimethylbicyclo[3.1.1]hept-2-en-4-one, 3,5,5-trimethylcyclohex-2-en-1-one, 3-methylcyclopent-2-en-1-one, (5S)-2-methyl-5-prop-1-en-2-ylcyclohex-2-en-1-one, (5R)-2-methyl-5-prop-1-en-2-ylcyclohex-2-en-1-one, 4-methylpent-3-en-2-one, 2-methyl-5-prop-1-en-2-ylcyclohex-2-en-1-one, 1-(1H-pyrrol-2-yl)ethenone, (5R)-5-methyl-2-propan-2-ylidenecyclohexan-1-one, 4-methylpent-3-en-2-one, 2-methyl-5-prop-1-en-2-ylcyclohex-2-en-1-one, 1-(1H-pyrrol-2-yl)ethenone, (5R)-5-methyl-2-propan-2-ylidenecyclohexan-1-one, 4-phenylbutan-2-one, 3-methylbutyl 3-oxobutanoate, 3-hydroxybutan-2-one, (Z)-3,4,5,6,6-pentamethylhept-3-en-2-one, 3-oxobutan-2-yl acetate, methyl 3-oxobutanoate, ethyl 3-oxobutanoate, (2R,5R)-2-methyl-5-prop-1-en-2-ylcyclohexan-1-one, 2-methyl-5-prop-1-en-2-ylcyclohexan-1-one, (2S,5S)-2-methyl-5-prop-1-en-2-ylcyclohexan-1-one, 2-ethyl-4,4-dimethylcyclohexan-1-one, 1-(3,3-dimethylcyclohexyl)ethanone, (2S,5S)-5-methyl-2-propan-2-ylcyclohexan-1-one, (2S,5R)-5-methyl-2-propan-2-ylcyclohexan-1-one, 2,2,5-trimethyl-5-pentylcyclopentan-1-one, 3,3,5-trimethylcyclohexan-1-one, 2-cyclopentylcyclopentan-1-one, (1S,4R,5R)-4-methyl-1-propan-2-ylbicyclo[3.1.0]hexan-3-one, 4-(2-methylbutan-2-yl)cyclohexan-1-one, 4,7,7-trimethylbicyclo[2.2.1]heptan-3-one, 6-methylhept-5-en-2-one, octan-2-one, (1S,4R)-2,2,4-trimethylbicyclo[2.2.1]heptan-3-one, heptan-2-one, 2,2,4-trimethylbicyclo[2.2.1]heptan-3-one, 5-methylheptan-3-one, octan-3-one, and mixtures thereof.

R. The apparatus according to any one of L, M, N, O, P or Q, wherein the volatile material comprises a mixture of volatile aldehydes selected from the group consisting of Accord A, Accord B and mixtures thereof.

S. A method of visually demonstrating efficacy of a volatile material for reducing malodor on surfaces, the method comprising the steps of:
a) providing a first inanimate surface in a first enclosed environment, at least a portion of the first inanimate surface is treated with a pH indicator, wherein the pH indicator has a first color and is capable of undergoing a change of color to a second color different from the first color upon contact with a pre-determined malodor;
b) providing a second inanimate surface in a second enclosed environment, at least a portion of the second inanimate surface is treated with the same pH indicator as is used to treat the first inanimate surface, each of the first and second inanimate surfaces comprising a permeable material;
c) providing a volatile material having a carbonyl containing compound into the second enclosed environment such that the volatile material vaporizes and deposits a carbonyl containing compound on at least a portion of the second inanimate surface; and
d) exposing both the first and second inanimate surfaces in their respective first and second environments to a malodor containing compound containing the pre-determined malodor, wherein the malodor containing compound is selected from the group consisting of an amine-containing compound and a thiol-containing compound;
wherein the carbonyl containing compound undergoes a nucleophilic addition in the presence of the malodor containing compound disposed on the at least a portion of the second inanimate surface such that the pH indicator disposed on the second permeable material exhibits a different color than the pH indicator disposed on the first inanimate surface.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of reducing malodor on surfaces, the method comprising the steps of:
   a) providing an apparatus in an environment including a surface comprising a permeable material having disposed thereon a malodor containing compound selected from the group consisting of: amine-containing compound and thiol-containing compound, wherein the apparatus includes a volatile material having a volatile carbonyl containing compound having a vapor pressure of at least 0.025 torr at 25 degrees Celsius; and
   b) exposing the volatile material to the environment without aerosol means such that the volatile carbonyl containing compound vaporizes from the apparatus and deposits on at least a portion of the surface;
   wherein the carbonyl containing compound undergoes a nucleophilic addition in the presence of the malodor containing compound, and
   wherein exposing the volatile material to the environment does not comprise emitting a non-volatile compound.

2. The method according to claim 1, further comprising a step (c) of neutralizing the malodor containing compound by a reaction product produced in step (b), thereby reducing the malodor on the surface.

3. The method according to claim 1, wherein the step of providing an apparatus comprises providing a reservoir for the volatile material, the reservoir including an opening and a membrane sealably covering the opening of the reservoir, wherein the membrane comprises a first surface in fluid contact with the volatile material and a second surface facing the environment and away from the volatile material.

4. The method according to claim 3, wherein the step of exposing the volatile material to the environment comprises wetting the membrane.

5. The method according to claim 1, wherein the vapor pressure of the volatile carbonyl containing compound is less than or equal to 30 torr at 25 degrees Celsius.

6. The method according to claim 1 wherein the volatile carbonyl containing compound is selected from the group consisting of: volatile aldehydes, ketones, and mixtures thereof.

7. The method according to claim 6, wherein the volatile carbonyl containing compound comprises at least one volatile aldehyde selected from the group consisting of: (E)-3-phenylprop-2-enal, benzaldehyde, 4-propan-2-ylbenzaldehyde, 4-methoxybenzaldehyde, (2E,6Z)-nona-2,6-dienal, (E)-hex-2-enal, (2E,6Z)-dodeca-2,6-dienal, non-2-enal, 2,4,6-trimethylcyclohex-3-ene-1-carbaldehyde; 3,5,6-trimethylcyclohex-3-ene-1-carbaldehyde, 3-(6,6-dimethyl-4-bicyclo [3.1.1]hept-3-enyl)-2,2-dimethylpropanal, nonanal, (E)-dec-4-enal, 2,6-dimethylhept-5-enal, (Z)-non-6-enal, 7-methoxy-3,7-dimethyloctanal, 3-(4-methylcyclohex-3-en-1-yl)butanal, 3,7-dimethyloct-6-enal, 2-methyldecanal, 2,4-dimethylcyclohex-3-ene-1-carbaldehyde, undec-10-enal, 4,8-dimethyldeca-4,9-dienal, octanal, undecanal, decanal, undec-9-enal, 6-methoxy-2,6-dimethylheptanal, 3-(6,6-dimethyl-4-bicyclo [3.1.1]hept-3-enyl)prop anal, 4,7-Methanoindan-1-carboxaldehyde and mixtures thereof.

8. The method according to claim 6, wherein the volatile carbonyl containing compound comprises at least one ketone selected from the group consisting of: 2,6,6-trimethylcyclohex-2-ene-1,4-dione, 4,7,7-trimethylbicyclo[2.2.1]heptane-2,3-dione, 1-phenylethanone, pentane-2,3-dione, 4-methoxy-2,5-dimethylfuran-3-one, 4-hydroxy-2,5-dimethylfuran-3-one, (1S,5S)-2,6,6-trimethylbicyclo[3.1.1]hept-2-en-4-one, (1R,5R)-2,6,6-trimethylbicyclo[3.1.1]hept-2-en-4-one, 3,5,5-trimethylcyclohex-2-en-1-one, 3-methylcyclopent-2-en-1-one, (5S)-2-methyl-5-prop-1-en-2-ylcyclohex-2-en-1-one, (5R)-2-methyl-5-prop-1-en-2-ylcyclohex-2-en-1-one, 4-methylpent-3-en-2-one, 2-methyl-5-prop-1-en-2-ylcyclohex-2-en-1-one, 1-(1H-pyrrol-2-yl)ethenone, (5R)-5-methyl-2-propan-2-ylidenecyclohexan-1-one, 4-methylpent-3-en-2-one, 2-methyl-5-prop-1-en-2-ylcyclohex-2-en-1-one, 1-(1H-pyrrol-2-yl)ethenone, (5R)-5-methyl-2-propan-2-ylidenecyclohexan-1-one, 4-phenylbutan-2-one, 3-methylbutyl 3-oxobutanoate, 3-hydroxybutan-2-one, (Z)-3,4,5,6,6-pentamethylhept-3-en-2-one, 3-oxobutan-2-yl acetate, methyl 3-oxobutanoate, ethyl 3-oxobutanoate, (2R,5R)-2-methyl-5-prop-1-en-2-ylcyclohexan-1-one, 2-methyl-5-prop-1-en-2-ylcyclohexan-1-one, (2S,5S)-2-methyl-5-prop-1-en-2-ylcyclohexan-1-one, 2-ethyl-4,4-dimethylcyclohexan-1-one, 1-(3,3-dimethylcyclohexyl)ethenone, (2S,5S)-5-methyl-2-propan-2-ylcyclohexan-1-one, (2S,5R)-5-methyl-2-propan-2-ylcyclohexan-1-one, 2,2,5-trimethyl-5-pentylcyclopentan-1-one, 3,3,5-trimethylcyclohexan-1-one, 2-cyclopentylcyclopentan-1-one, (1S,4R,5R)-4-methyl-1-propan-2-ylbicyclo [3.1.0]hexan-3-one, 4-(2-methylbutan-2-yl)cyclohexan-1-one, 4,7,7-trimethylbicyclo[2.2.1]heptan-3-one, 6-methylhept-5-en-2-one, octan-2-one, (1S,4R)-2,2,4-trimethylbicyclo[2.2.1]heptan-3-one, heptan-2-one, 2,2,4-trimethylbicyclo [2.2.1]heptan-3-one, 5-methylheptan-3-one, octan-3-one, and mixtures thereof.

9. The method according to claim 1 wherein the volatile carbonyl containing compound is in an amount of greater than or equal to 0.01% to less than or equal to 25%, by weight of the volatile material.

10. The method according to claim 1, wherein the permeable material is selected from the group consisting of: fabrics, drywall, wovens, paper, natural polymers, synthetic polymers and inorganic materials and mixtures thereof.

11. The method according to claim 1, wherein the volatile material comprises a volatile aldehyde mixture selected from the group consisting of Accord A, Accord B and mixtures thereof.

* * * * *